United States Patent
Gross et al.

(10) Patent No.: US 7,319,143 B2
(45) Date of Patent: Jan. 15, 2008

(54) GENETICALLY-ENGINEERED MHC MOLECULES

(75) Inventors: Gideon Gross, Korazim (IL); Alon Margalit, Western Galilee (IL)

(73) Assignee: Gavish-Galilee Bio Application Ltd., Rosh Pina (IL)

( * ) Notice: Subject to any disclaimer, the term of this patent is extended or adjusted under 35 U.S.C. 154(b) by 833 days.

(21) Appl. No.: 10/297,060

(22) PCT Filed: May 31, 2001

(86) PCT No.: PCT/IL01/00506

§ 371 (c)(1),
(2), (4) Date: Dec. 2, 2002

(87) PCT Pub. No.: WO01/91698

PCT Pub. Date: Dec. 6, 2001

(65) Prior Publication Data

US 2004/0137562 A1    Jul. 15, 2004

(51) Int. Cl.
*C12N 5/00* (2006.01)
*C07H 21/04* (2006.01)
*C07K 1/00* (2006.01)

(52) U.S. Cl. .................... 536/23.4; 536/23.5; 435/325; 530/402; 530/403

(58) Field of Classification Search .................... None
See application file for complete search history.

(56) References Cited

FOREIGN PATENT DOCUMENTS

| WO | WO 92/10591 A | 6/1992 |
|---|---|---|
| WO | WO 97/08328 | 3/1997 |
| WO | WO 97/20938 A | 6/1997 |

OTHER PUBLICATIONS

Geiger et al. "The TCR zeta-Chain Immunoreceptor Tyrosine-Based Activation Motifs Are Sufficient for the Activation and Differentiation of Primary T Lymphocytes" *The Journal of Immunology* 1999, 162: 5931-5939.
Eshhar et al. "Specific Activation ad Targeting of Cytotoxic Lymphocytes Through Chimeric Single Chains Consisting of Antibody-binding Domains and the Gamma or Zeta Subunits of the Immunoglobulin and T-cell Receptors" *Pro. Natl. Acad. Sci USA* 90: 720-724 1(1999).
Gross et al. "Chimaeric T-cell Reeptors Specific to a B-Lymphoma Idiotype: A model for Tumour Immunotherapy" *Biochem Soc Trans* 23:1079-82.
Gross et al. "Expression of Immunoglobulin-T-cell Receptor Chimeric Molecules as Functional receptors with Antibody-Type Specificity" *Proc. Natl. Acad. Sci USA* 86:10024-8, 12(1989).
HWU et al. "Lysis of Ovarian Cancer Cells by Human Lymphocytes Redirected with a Chimeric Gene Composed of an Antibody Variable Region and the Fc Receptor Gamma Chain" *The Journal of Experimental Medicine* 178: 361-366, 7(1993).
Irving et al. "The Cytoplasmic Domain of the T Cell Receptor Zeta Chain is Sufficient to Couple to Receptor-Associated Signal Transduction Pathways" *Cell* 64:891-901, 3(1991).
Romeo et al. "Cellular Immunity to HIV Activated by CD4 Fused to Cell or Fc Receptor Polypeptides" *Cell* 64: 1037-1046, 2(1991).
Uger et al. "Creating CTL Targets with Epitope-Linked Beta2-Microglobulin Constructs" *The Journal of Immunology* 160:1598-1605, (1998).
Uger et al. "Covalent Linkage to Beta2-Microglobulin Enhances the MHC Stability and Antigenicity of Suboptimal CTL Epitopes" *The Journal of Immunology* 162: 6024-6028, (1999).
White et al. "Soluble Class I MHC with Beta2-Microglobulin Covalently Linked Peptides: Specific Binding to a T Cell Hybridoma" *The Journal of Immunology* 162: 2671-2676, (1999).
Hombach A et al "Chimeric anti-TAG72 receptors with immunoglubulin constant domains and gamma or zeta signaling chains" International Journal of Molecular Medicine. (Jul. 1998) vol. 2, No. 1, pp. 99-103.
Margalit Alon et al "Chimeric beta2 microglobulin/CD3zeta polypeptides expressed in T cells conver MHC class I peptide ligands into T cell activation receptors: A potential tool for specific targeting of pathogenic CD8+ T cells" International Immunology (Nov. 2003) vol. 15, No. 11, pp. 1379-1387.
Moritz D et al "A Spacer Region Between the Single Chain Anti-body- and the CD3 zeta-Chain Domain of Chimeric T Cell Receptor Components is Required for Efficient Ligand Binding and Signalling Activity" Gene Therapy (Oct. 1, 1995) vol. 2, No. 8, pp. 539-546.

*Primary Examiner*—Christina Chan
*Assistant Examiner*—F. Pierre VanderVegt
(74) *Attorney, Agent, or Firm*—Browdy & Neimark, PLLC

(57) ABSTRACT

The invention provides DNA molecules encoding a chimeric polypeptide comprising (a) a component of a MHC molecule capable of association on a cell surface with an endogenous MHC molecule component of the same class, and (b) an intracellular region of a signal transduction element capable of activating T cells. Component (a) may be a monomorphic component and is preferably beta 2-microglobulin, or a polymorphic class I or class II component. The signal transduction element (b) capable of activating T cells may be a component of T-cell receptor CD3, preferably the CD3 zeta (zeta) polypeptide, a B cell receptor polypeptide or an Fc receptor polypeptide. Immune cells such as a CTLs expressing said chimeric MHC molecules specifically eliminate or inactivate harmful T cells and are useful for treating graft rejection and autoimmune diseases.

16 Claims, 8 Drawing Sheets

Figure 3

Human β2m

```
atgtctcgct ccgtggcctt agctgtgctc gcgctactct ctctttctgg
cctggagggc atccagcgta ctccaaagat tcaggtttac tcacgtcatc
cagcagagaa tggaaagtca aatttcctga attgctatgt gtctgggttt
catcaatccg acattgaagt tgacttactg aagaatggag agagaattga
aaaagtggag cattcagact tgtctttcag caaggactgg tctttctatc
tcttgtacta cactgaattc accccactg aaaagatga gtatgcctgc
cgtgtgaacc atgtgacttt gtcacagccc aagatagtta agtgggatcg
agacatgtaa
```

Mouse CD3 ζ chain

```
ctctgctact tgctagatgg aatcctcttc atctacggag tcatcatcac
agccctgtac ctgagagcaa aattcagcag gagtgcagag actgctgcca
acctgcagga ccccaaccag ctctacaatg agctcaatct agggcgaaga
gaggaatatg acgtcttgga gaagaagcgg gctcgggatc agagatggg
aggcaaacag cagaggagga ggaaccccca ggaaggcgta tacaatgcac
tgcagaaaga caagatggca gaagcctaca gtgagatcgg cacaaaggc
gagaggcgga gaggcaaggg gcacgatggc ctttaccagg gtctcagcac
tgccaccaag gacacctatg atgccctgca tatgcagacc ctggcccctc
gctaa
```

Chimeric hβ2m/ζ

```
tctagagccg agatgtctcg ctccgtggcc ttagctgtgc tcgcgctact
ctctctttct ggcctggagg gcatccagcg tactccaaag attcaggttt
actcacgtca tccagcagag aatggaaagt caaatttcct gaattgctat
gtgtctgggt ttcatcaatc cgacattgaa gttgacttac tgaagaatgg
agagagaatt gaaaaagtgg agcattcaga cttgtctttc agcaaggact
ggtctttcta tctcttgtac tacactgaat tcaccccac tgaaaaagat
gagtatgcct gccgtgtgaa ccatgtgact ttgtcacagc ccaagatagt
taagtgggat cgagacatgc tgagatggga gcctcgagc cagcccacca
tccccatcct ctgctacttg ctagatggaa tcctcttcat ctacggagtc
atcatcacag ccctgtacct gagagcaaaa ttcagcagga gtgcagagac
tgctgccaac ctgcaggacc ccaaccagct ctacaatgag ctcaatctag
ggcgaagaga ggaatatgac gtcttggaga agaagcgggc tcgggatcca
gagatgggag gcaaacagca gaggaggagg aaccccagg aaggcgtata
caatgcactg cagaaagaca gatggcaga agcctacagt gagatcggca
caaaaggcga gaggcggaga ggcaagggc acgatggcct ttaccagggt
ctcagcactg ccaccaagga cacctatgat gccctgcata tgcagaccct
ggcccctcgc taagaattc
```

Figure 6
A.
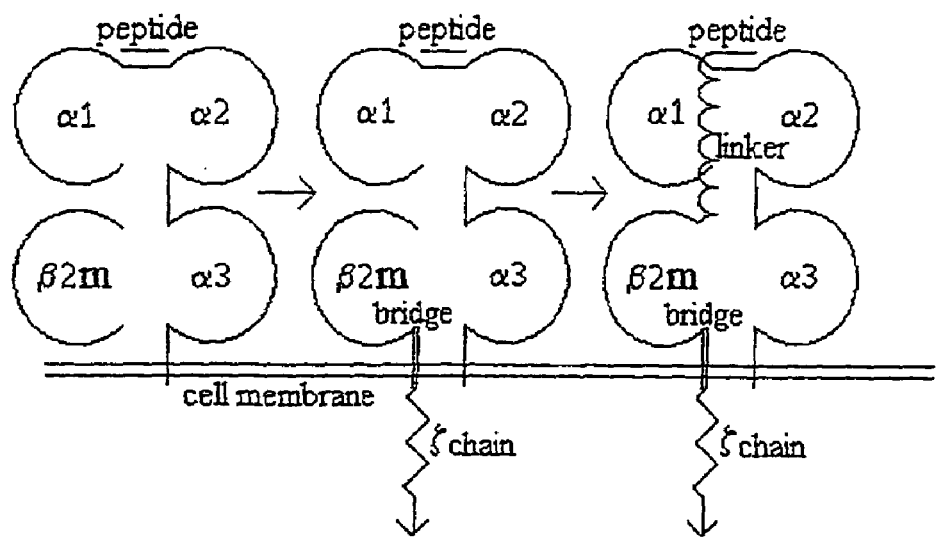
B.
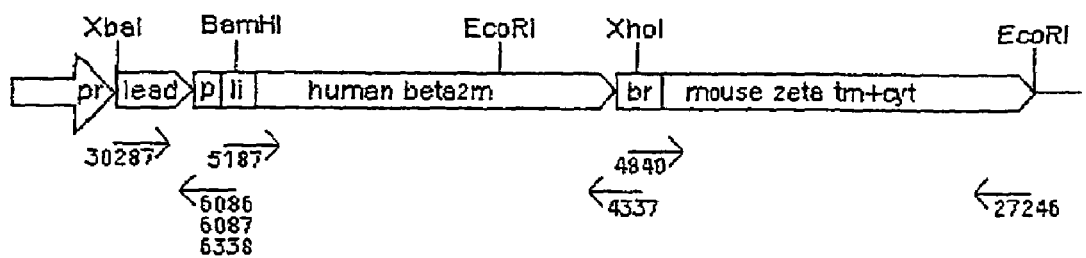

Figure 7

The chimeric NP/hβ2/ζ gene
```
tctagagccg agatgtctcg ctccgtggcc ttagctgtgc tcgcgctact
ctctctttct ggcctggagg gcagtgatta tgaagggcgg ttgatcggag
gtggcggatc cggaggtggt tctggtggag gttcgatcca gcgtactcca
aagattcagg tttactcacg tcatccagca gagaatggaa agtcaaattt
cctgaattgc tatgtgtctg ggtttcatca atccgacatt gaagttgact
tactgaagaa tggagagaga attgaaaaag tggagcattc agacttgtct
ttcagcaagg actggtcttt ctatctcttg tactacactg aattcacccc
cactgaaaaa gatgagtatg cctgccgtgt gaaccatgtg actttgtcac
agcccaagat agttaagtgg gatcgagaca tgctgagatg ggagccctcg
agccagccca ccatccccat cctctgctac ttgctagatg gaatcctctt
catctacgga gtcatcatca cagccctgta cctgagagca aaattcagca
ggagtgcaga gactgctgcc aacctgcagg accccaacca gctctacaat
gagctcaatc tagggcgaag agaggaatat gacgtcttgg agaagaagcg
ggctcgggat ccagagatgg gaggcaaaca gcagaggagg aggaaccccc
aggaaggcgt atacaatgca ctgcagaaag acaagatggc agaagcctac
agtgagatcg gcacaaaagg cgagaggcgg agaggcaagg ggcacgatgg
cctttaccag ggtctcagca ctgccaccaa ggacacctat gatgccctgc
atatgcagac cctggcccct cgctaagaat tc
```

The Chimeric Ha/β2m/ζ gene
```
tctagagccg agatgtctcg ctccgtggcc ttagctgtgc tcgcgctact
ctctctttct ggcctggagg gctttgagag tactggtaat ctaattggag
gtggcggatc c
```

The Chimeric IB/β2m/ζ gene
```
tctagagccg agatgtctcg ctccgtggcc ttagctgtgc tcgcgctact
ctctctttct ggcctggagg gcctctacct ggtgtgtggg gagcgtggcg
gaggtggcgg atcc
```

FIG. 10b

HLA-DRα

```
atggccataa gtggagtccc tgtgctagga ttttcatca tagctgtgct
gatgagcgct caggaatcat gggctatcaa agaagaacat gtgatcatcc
aggccgagtt ctatctgaat cctgaccaat caggcgagtt tatgtttgac
tttgatggtg atgagatttt ccatgtggat atggcaaaga aggagacggt
ctggcggctt gaagaatttg gacgatttgc cagctttgag gctcaaggtg
cattggccaa catagctgtg gacaaagcca acctggaaat catgacaaag
cgctccaact atactccgat caccaatgta cctccagagg taactgtgct
cacgaacagc cctgtggaac tgagagagcc caacgtcctc atctgtttca
tcgacaagtt caccccacca gtggtcaatg tcacgtggct tcgaaatgga
aaacctgtca ccacaggagt gtcagagaca gtcttcctgc caggggaaga
ccaccttttc cgcaagttcc actatctccc cttcctgccc tcaactgagg
acgtttacga ctgcagggtg gagcactggg gcttggatga gcctcttctc
aagcactggg agtttgatgc tccaagccct ctcccagaga ctacagagaa
cgtggtgtgt gccctgggcc tgactgtggg tctggtggcc atcattattg
ggaccatctt catcatcaag ggagtgcgca aaagcaatgc agcagaacgc
aggggcctc tgtaa
```

Chimeric DRα/ζ

```
ctcgaggcgc caagaagaa aatggccata agtggagtcc ctgtgctagg
attttcatc atagctgtgc tgatgagcgc tcaggaatca tgggctatca
aagaagaaca tgtgatcatc caggccgagt tctatctgaa tcctgaccaa
tcaggcgagt ttatgtttga ctttgatggt gatgagattt tccatgtgga
tatggcaaag aaggagacgg tctggcggct tgaagaattt ggacgatttg
ccagctttga ggctcaaggt gcattggcca acatagctgt ggacaaagcc
aacctggaaa tcatgacaaa gcgctccaac tatactccga tcaccaatgt
acctccagag gtaactgtgc tcacgaacag ccctgtggaa ctgagagagc
ccaacgtcct catctgtttc atcgacaagt tcaccccacc agtggtcaat
gtcacgtggc ttcgaaatgg aaaacctgtc accacaggag tgtcagagac
agtcttcctg ccagggaag accaccttt ccgcaagttc cactatctcc
ccttcctgcc ctcaactgag gacgtttacg actgcagggt ggagcactgg
ggcttggatg agcctcttct caagcactgg gtctgctacc ttctagatgg
aatcctcttc atctacggag tcatcatcac agccctgtac ctgagagcaa
aattcagcag gagtgcagag actgctgcca acctgcagga ccccaaccag
ctctacaatg agctcaatct agggcgaaga gaggaatatg acgtcttgga
gaagaagcgg gctcgggatc cagagatggg aggcaaacag cagaggagga
ggaacccca ggaaggcgta taatgcac tgcagaaaga caagatgca
gaagcctaca gtgagatcgg cacaaaggc gagaggcgga gaggcaaggg
gcacgatggc ctttaccagg gtctcagcac tgccaccaag gacacctatg
atgccctgca tatgcagacc ctggccctc gctaagaatt c
```

GENETICALLY-ENGINEERED MHC MOLECULES

FIELD OF THE INVENTION

The present invention is in the field of Immunology and relates to an immunotherapeutic approach designed to specifically eliminate or inactivate undesired harmful T cells. In particular, the invention relates to DNA constructs encoding chimeric molecules comprising a MHC component, and a signal transduction element component, and to cells transfected with such DNA molecules that are useful in the prevention and/or treatment of T-cell mediated disorders and conditions such as graft rejection and autoimmune diseases.

ABBREVIATIONS: APC—antigen-presenting cell; $\beta_2$m—$\beta_2$ microglobulin; CTL—cytotoxic T lymphocyte; EAE—experimental autoimmune encephalomyelitis; Ha—hemagglutinin; HLA—human leukocyte antigen (=human MHC); IB—insulin B chain; IDDM—insulin-dependent diabetes mellitus; Ig—immunoglobulin; ITAM—immunoreceptor tyro sine-based activation motif; mAb—monoclonal antibody; MHC—major histocompatibility complex; MS—multiple sclerosis; NP—nucleoprotein; RT-PCR—reverse transcriptase-polymerase chain reaction; TCR—T-cell receptor; $T_H$—T helper cells.

BACKGROUND OF THE INVENTION

Lymphocytes are the main cells of the immune system responsible for acquired immunity and the immunologic characteristics of diversity, specificity, memory and self/nonself recognition. Lymphocytes can be broadly divided into B cells, characterized by the presence of membrane-bound immunoglobulin (antibody) molecules which serve as receptors for, and can bind, soluble antigens; and T cells, characterized by the presence of membrane-bound receptor molecules (TCR, for T-cell receptor), which recognize and bind antigen only when the antigen is associated with a self-molecule encoded by genes within the major histocompatibility complex (MHC). The MHC is referred to as the H-2 complex in mice and as the HLA (for human leukocyte antigen) complex in humans.

T-cell recognition of antigen is the basis of the adaptive immune response, which is the ability of the immune system to selectively recognize, neutralize and obliterate infectious pathogens or pathological cells. Effector T cells generated in response to antigen are responsible for cell-mediated immunity. All T-cell subpopulations express the TCR, but they can be distinguished by the presence of one or the other of two membrane glycoprotein molecules on their surfaces (surface antigens), CD4 or CD8, and their role in the immune response. Thus, two major subpopulations of T cells can be characterized: the CD4$^+$ or helper T cells ($T_H$), which facilitate the activities of other cell types, and the CD8$^+$ or cytotoxic T lymphocytes (CTL), which can directly kill abnormal or infected cells.

CD4$^+$ T cells are further divided into $T_H1$ inflammatory T cells, which secrete various cytokines ($T_H1$ response) that activate mainly T cytotoxic cells and macrophages responsible for the intracellular destruction of phagocytosed microorganisms, and $T_H2$ T cells, which secrete various cytokines ($T_H2$ response) that activate B cells to produce antibodies. CD8$^+$ T cells generally function as CTLs. Another T-cell related lymphocyte subset is the natural killer cells (NK), which are large, granulated lymphocytes displaying cytotoxic activity against a wide variety of tumor and other abnormal cells.

T-cell recognition is mediated by direct interaction of the TCR with an antigenic peptide displayed by a MHC product on an antigen-presenting cell (APC). As a result of specific interaction between TCR of a T lymphocyte that has not yet interacted with antigen (naive or unprimed cell) with MHC molecules displaying antigenic peptides on a professional APC (e.g. dendritic cells, macrophages, B cells), the T cell is activated and it proliferates and eventually differentiates to produce effector cells, which function as $T_H$ cells or CTLs to eliminate the antigen, and memory cells, which are responsible for the life-long immunity observed for many pathogens.

In mammals, there are two types of MHC molecules: MHC class I molecules, which are present on almost all nucleated cells in the body and are recognized by CD8$^+$ cells, and MHC class II molecules, which are mainly expressed on professional APCs of the immune system and are recognized by CD4$^+$ cells. Thus, CD8$^+$ T cells, which generally function as CTLs, are said to be class I restricted, and CD4$^+$ T cells, which generally function as $T_H$ cells, are said to be class II restricted.

Class I MHC molecules are composed of a polymorphic heavy chain ($\alpha$) non-covalently associated with a monomorphic (in humans) non-MHC encoded light chain protein of about 12 kDa, termed $\beta_2$ microglobulin ($\beta_2$m). The heavy $\alpha$ chain is a polymorphic transmembrane glycoprotein of about 45 kDa consisting of 3 extracellular domains, each containing about 90 amino acids ($\alpha_1$ at the N-terminus, $\alpha_2$ and $\alpha_3$), a transmembrane region of about 40 amino acids and a cytoplasmic tail of about 30 amino acids. The $\alpha_1$ and $\alpha_2$ domains, the membrane distal domains, form the peptide-binding groove or cleft having a sufficient size to bind a peptide of 8-10 amino acids, whereas the $\alpha_3$ domain is proximal to the plasma membrane. $\beta_2$m has a single immunoglobulin (Ig)-like domain, not anchored to the plasma membrane, and interacts mainly with the $\alpha_3$ chain, which also possesses a characteristic Ig fold. In humans, there are three $\alpha$ chain genes, called HLA-A, HLA-B and HLA-C, for each of which multiple alleles have been identified. In mice, there are three $\alpha$ chain genes, called H-2K, H-2D and H-2L. CD8$^+$ T cells recognize peptides in the context of MHC class I molecules.

Class II MHC molecules contain two different polypeptide chains, a 33-kD $\alpha$ chain and a 28-kDa $\beta$ chain, which associate by noncovalent interactions. Like class I MHC molecules, class II MHC molecules are membrane-bound glycoproteins that contain extracellular domains, a transmembrane segment and a cytoplasmic tail. Each chain in these noncovalent heterodimeric complexes contains two extracellular domains: $\alpha_1$ and $\alpha_2$ domains and $\beta_1$ and $\beta_2$ domains. The membrane-distal domain of a class II molecule is composed of the $\alpha1$ and $\beta1$ domains and forms the peptide-binding groove or cleft having a sufficient size to bind a peptide, which is typically of 13-18 amino acids. The membrane-proximal domains, $\alpha2$ and $\beta2$, have structural similarities to Ig constant (C) domains. Three pairs of class II $\alpha$ and $\beta$ chain genes exist in humans, known as HLA-DR, HLA-DP and HLA-DQ. The highest level of polymorphism is documented for HLA-DR. This polymorphism is solely contributed by the DR$\beta$ chain, as DR$\alpha$ is monomorphic. In mice, the pairs of genes are called H-2IA and H-2IE. CD4$^+$ $T_H$ cells recognize peptides in the context of class II MHC molecules.

All T cells bind their specific MHC::peptide antigen via clone-specific or clonotypic TCR molecules. TCRs are disulfide-linked heterodimeric transmembrane proteins made of α and β chains. The N-terminal variable (V) domains of these chains, which together form the antigen-binding site, are similar to those of Ig variable (V) chains, whereas the membrane-anchored C-terminal domains are analogous to Ig constant (C) domains.

On the T-cell membrane, the clonotypic TCR associates non-covalently with CD3, forming the TCR-CD3 membrane complex. CD3, the signal transduction element of the TCRs, is composed of a group of invariant proteins called gamma (γ), delta (δ), epsilon (ε), zeta (ζ) and eta (η) chains. The γ, δ and ε chains are structurally-related, each containing an Ig-like extracellular constant domain followed by a transmembrane region and a cytoplasmic domain of more than 40 amino acids. The ζ and η chains have a distinctly different structure: both have a very short extracellular region of only 9 amino acids, a transmembrane region and a long cytoplasmic tail containing 113 and 115 amino acids in the ζ and η chains, respectively. The invariant protein chains in the CD3 complex associate to form noncovalent heterodimers of the ε chain with a γ chain (εγ) or with a δ chain (εδ) or of the ζ and η chain (ζη), or a disulfide-linked homodimer of two ζ chains (ζζ). About 90% of the CD3 complex incorporate the ζζ homodimer.

The cytoplasmic regions of the CD3 chains contain a motif designated the immunoreceptor tyrosine-based activation motif (ITAM). This motif is found in a number of other: receptors including the Ig-α/Ig-β heterodimer of the B-cell receptor complex and Fc receptors for IgE and IgG. The ITAM sites have been shown to associate with cytoplasmic tyrosine kinases and to participate in signal transduction following TCR-mediated triggering. In CD3, the γ, δ and ε chains each contain a single copy of ITAM, whereas the ζ and η chains harbour three ITAMs in their long cytoplasmic regions. Indeed, the ζ and η chains have been ascribed a major role in T cell activation signal transduction pathway (Howe and Weiss, 1995; Sherman and Chattopadhyay, 1993).

In mammals, T cell maturation occurs in the thymus. During maturation, a distinct mechanism operates to ensure positive selection, namely that αβ TCRs expressed in a given individual cell will recognize and bind to self-MHC molecules, as well as negative selection, namely to eliminate those T cells bearing high affinity TCRs which may interact with self-MHC molecules alone or self-antigens plus self-MHC molecules, that would pose the threat of an autoimmune response if they matured. Hence, the mature T-cell repertoire can provide an adequate defense against pathogens, while avoiding response against self-antigens. However, peripheral tissue antigens often fail to be adequately presented in the thymus, and potentially self-reactive T cells do succeed to exit the thymus, while downstream mechanisms, which induce peripheral tolerance are not always sufficient to inactivate these potentially harmful T cells. In addition, no mechanism has evolved to eliminate or inactivate T cells capable of reacting against foreign MHC allelic products, referred to as alloreactive cells. As a result, the action of harmful T cells may inflict severe damage and may be associated with life-threatening situations commonly associated with T-cell mediated diseases and conditions such as autoimmune diseases and transplantation, and with responses against innocuous foreign antigens, resulting in hypersensitivity reactions such as allergy and asthma.

Autoimmune disorders are characterized by reactivity of the immune system to an endogenous antigen, with consequent injury to tissues. More than 80 chronic autoimmune diseases have been characterized that affect virtually almost every organ system in the body. The most common autoimmune diseases are insulin-dependent diabetes mellitus (IDDM), multiple sclerosis (MS), systemic lupus erythematosus (SLE), rheumatoid arthritis, several forms of anemia (pernicious, aplastic, hemolytic), thyroiditis, and uveitis. Autoimmune disorders are far more prevalent in women and are among the top 10 causes of death of young and middle-aged women in the U.S.A.

Autoimmune diseases result from sustained adaptive immune responses mounted against innocuous self-antigens. The effector mechanisms that eventually cause tissue damage and disease are most likely those that take part in normal adaptive responses, and include production of specific antibodies, generation of immune complexes, inflammatory and cytotoxic T cells and activated macrophages.

The role of T cells in autoimmune diseases has been extensively studied in MS, a chronic inflammatory disease of the central nervous system (CNS) and its rodent model experimental autoimmune encephalomyelitis (EAE), (for review, see Hafler and Weiner, 1995). In MS, activated $CD4^+$ T cells found in the central nervous system (CNS) display specificity to a number of abundant CNS proteins, including myelin basic protein (MBP), proteolipid protein (PLP), myelin oligodendrocyte-associated protein (MOG) and S-100. Susceptibility to MS is associated with the HLA-DR2 haplotype approximately 50-70% of MS patients carry the DR2 allele, which is found in only 20-30% of normal individuals. This association has enabled, for example, the identification of immunodominant MBP peptides using panels of HLA-DR2-restricted T cell clones (Wucherpfennig, et al., 1991).

A large bulk of data has also been accumulated in IDDM along with its non-obese diabetic (NOD) mouse model. In IDDM, $CD4^+$ T cell autoantigens include insulin, GAD (glutamic acid decarboxylase) 65, GAD67, hsp (heat-shock protein) 65, and ICA (islet-cell antigen) 69 (Roep, 1996). Recently, a study of the NOD mouse system, which employed a novel screening strategy, has enabled the identification of an insulin B-chain peptide as the first $CD8^+$ T cell epitope in an autoimmune disease (Wong, et al., 1999).

In summary, a limited number of peptides derived from proteins involved in autoimmune diseases are associated with the onset of the disease. The immune responses to self-antigens are maintained by the persistent activation of self-reactive T cells. Removal of T cell populations that are associated with the autoimmune response should lead to prevention and/or cure of the disease. This model was demonstrated in the NOD mice, where the removal of T-cell populations that recognize proinsulin II, prevented the onset of IDDM (French, et al., 1997).

Allograft rejection typically results from an overwhelming adaptive immune response against foreign organ or tissue. It is the major risk factor in organ transplantation and is the cause of post-transplantation complications. A major complication associated with bone marrow (BM) transplantation, known as graft-versus-host (GVH) reaction or graft-versus-host disease (GVHD), occurs in at least half of patients when grafted donor lymphocytes, injected into an allogeneic recipient whose immune system is compromised, begin to attack the host tissue, and the host's compromised state prevents an immune response against the graft Alloreactivity is complex and involves many cell types as well as inflammatory factors. It is largely mediated by both $CD8^+$ (CTL) and CD4+ (T$_H$) T cells (for review, see Douillard et al., 1999; Hernandez-Fuentes et al., 1999; Pattison and Krensky, 1997).

Allograft rejection results from proper recognition of foreign MHC and activation of the adaptive immune system and is carried out by direct or indirect pathways. The direct pathway, where T-cell receptors directly recognize intact allo-MHC with or without bound peptides on the surface of target cells, apparently accounts for most of the CTL function. The indirect pathway, where T-cell receptors recognize MHC allopeptides after processing and presentation, leads to the activation of T helper cells. These cells provide the necessary signals for the growth and maturation of effector CTLs and B cells leading to rejection (Sherman and Chattopadhyay, 1993; Watschinger, 1995).

The actual role of specific peptides in direct allorecognition is ambiguous. Some studies demonstrate that allorecognition is peptide-independent (Mullbacher et al., 1999; Smith et al., 1997), while others imply that specific peptides do contribute to allorecognition (Wang, et al., 1998). Allorecognition may, therefore, comprise peptide-independent, peptide-dependent or peptide-specific interactions.

Ideally, treatment of autoimmune diseases should reduce only the autoimmune response while leaving the rest of the immune system intact. In the absence of such treatments, current therapies of autoimmune diseases include non-immune-specific treatments via a broad spectrum of immunosuppressive drugs such as corticosteroids, cyclosporine A, methotrexate and tacrolimus (FK506). However, these agents have severe side effects such as "generalized immunosuppression" and toxicity.

Successful transplant engraftment and effective treatment of autoimmune diseases would be greatly facilitated by tolerizing, inactivating or eliminating harmful, or potentially harmful, T-cells. In both cases, specificity (or at least high selectivity) of the therapy is mandatory if severe side effects are to be minimized. For maximal efficacy and broad applicability, anti-T cell protocols are to target the whole repertoire of (allo or auto)specific T cell clones, and to act independently of HLA identity. Indeed, design and evaluation of specific treatment strategies have been the objective of numerous studies in both these fields. Among the approaches that were explored, are anti-T cell idiotypic manipulation (Bluestone et al., 1986), reduction of antigen presentation by the graft (Carpenter et al., 1976; Faustman, 1995) and suppression of T cell precursors by veto cells (Miller et al., 1988; Reich-Zeliger et al., 2000; Thomas et al., 1991).

Identification of potential autoantigens and characterization of autoantigen-specific T cell clones, mainly in MS (or EAE) and IDDM, have prompted active research aimed at developing specific immunotherapies to autoimmune diseases. Experimental therapeutic approaches include T-cell vaccination with autoreactive T cells (Ben-Nun and Cohen, 1981) or their TCR peptides (Howell et al., 1989; Vandenbark et al. 1991), tolerance induction by oral antigens (reviewed in Hafler and Weiner, 1995), peptide blockade of MHC molecules by specific peptides associated with the disease or their analogues (Elias et al., 1991; Windhagen et al., 1995), and monoclonal antibody treatment However, wide clinical applicability of these approaches still has to be demonstrated. Undoubtedly, novel solutions are to be constantly pursued so that accumulating knowledge and understanding of the immune system are eventually reduced to wide medical practice.

Specific direction of an immune intervention procedure against the pool of auto-or allo-specific T-cell clones demands a well-defined structural or functional common denominator which can serve as an identification tag for this pool. For example, the concept of vaccination with TCR peptides or whole autoreactive T cells (Howell, et al., 1989; Vandenbark, et al., 1991) is based on the observation that encephalitogenic T cells in EAE utilize only a restricted set of germ-line TCR Vα and Vβ genes, hence, their TCR amino acid sequences constitute a potential (although not fully specific) marker. However, autoreactive T cell clones isolated in MS are more promiscuous in their TCR usage and are thus less accessible to this strategy. The trivial common denominator of the whole panel of T cell clones recognizing a given MHC::peptide ligand is the ligand itself, irrelevant of TCR gene products of those clones. The problem is how this understanding can be exploited so that those cells can be specifically targeted for therapy. A novel mechanism, devised to trigger a potent reaction against those T cells following their specific interaction with the ligand is a likely solution. This can only be achieved if the ligand is engineered to be linked to an adequate effector function, activated upon its engagement with specific TCRs.

In recent years, the inventors (Eshhar et al., 1993; Gross et al., 1995; Gross et al., 1989; Hwu, et al., 1993) and others (reviewed in Gross and Eshhar, 1992), have demonstrated that genetic engineering enables redirecting T cell recognition at will via chimeric activation receptors. This was accomplished by replacement of the ligand-binding domain of a T-cell receptor, with binding domains derived from other receptor molecules. Other studies have shown that reciprocal substitution of transmembrane and intracellular domains of surface receptors with those of different molecules involved in T-cell activation signal transduction leads to a corresponding change in the pattern of response to the same signal. The transmembrane and cytoplasmic regions of the CD3 ζ chain or Ig Fc receptor γ chain have been frequently used in such experiments, proving most powerful in this regard (e,g. Eshhar et al., 1993; Irving and Weiss, 1991; Letourneur and Klausner, 1991; Romeo and Seed, 1991).

A number of publications disclose chimeric receptors comprising a CD3 ζ chain and an extracellular binding domain. For example, Seed et al., in U.S. Pat. No. 5,843,728, disclose chimeric receptors comprising the extracellular domain of CD4 fused to an intracellular portion of a TCR CD3 ζ or η chain, a B-cell receptor polypeptide or an Fc receptor polypeptide. T lymphocytes expressing these chimeras would recognize and kill cells expressing HIV gp120.

U.S. Pat. No. 5,855,740 and U.S. Pat. No. 5,834,266 disclose chimeras comprising an intracellular CD3 ζ chain and an extracellular domain capable of specifically binding to at least one ligand. U.S. Pat. No. 5,359,046 discloses chimeras optionally containing an intracellular CD3 ζ chain fused to extracellular domains derived from CD4, CD8, Ig or single-chain antibody. U.S. Pat. No. 5,712,149 discloses chimeric costimulatory receptors whose intracellular domain is derived from CD2 or CD28 and may, in addition, comprise a CD3 ζ chain domain.

SUMMARY OF THE INVENTION

It is an object of the present invention to provide a novel concept and means for specific removal, by elimination or inactivation, of undesired T cells such as autoreactive T cells causing autoimmune diseases and alloreactive T cells causing transplant rejection or GVHD.

The present invention is based on the principle that MHC products can be genetically engineered into T-cell activation molecules and that, when these MHC components are monomorphic, the engineered molecules can act independently of MHC identity. Thus, a MHC component genetically engrafted with intracellular structural elements responsible for transduction of T cell activation signals, may be functionally expressed on the membrane of T cells, particularly cytotoxic T lymphocytes (CTLs), together with relevant antigenic peptides, and these modified T cells (effector cells) will target specific, harmful T cells bearing the antigen receptors (target T cells) and will cause lysis or inactivation of the undesired T cells.

The present invention thus relates, in one aspect, to a DNA molecule encoding a chimeric polypeptide comprising (a) a component of a MHC molecule capable of association on a cell surface with an endogenous MHC molecule component of the same class, and (b) an intracellular region of a signal transduction element capable of activating T cells and, optionally, an antigenic peptide related to an autoimmune disease linked to said chimeric polypeptide by a peptide linker.

According to the present invention, once MHC components are supplemented with a signal transduction element capable of activating T cells such as the transmembranal and cytoplasmic regions of the CD3 ζ chain, they will be endowed with the capacity to transduce T-cell activation signal. If expressed by CTLs, these chimeric MHC molecules can function as traps: T cells interacting with them (while occupied with antigenic peptides) are destined to be lysed. In other words, such a manipulation is expected to provoke an 'inverted' response: from ligand to TCR.

In further aspects, the invention relates to a vector comprising a DNA molecule of the invention and to cells, particularly T cells such as CTLs, expressing a chimeric polypeptide encoded by the DNA molecule of the invention.

In still a further aspect, the invention relates to methods for prevention and/or treatment of T-cell mediated diseases or conditions such as autoimmune diseases and transplant rejection, which comprises administering to a patient in need thereof immune cells, particularly CTLs, that express a chimeric polypeptide encoded by the DNA molecule of the invention.

BRIEF DESCRIPTION OF THE FIGURES

FIG. 3 shows the DNA sequences of the chimeric $h\beta_2m/\zeta$ gene and its separate components. Upper panel. DNA sequence of the coding region of the human $\beta_2m$ gene (SEQ ID NO:1) (from GenBank Accession AF072097) Middle panel: The region encoding mouse CD3 ζ chain (SEQ ID NO:2) transmembranal and cytoplasmic domains (from GenBank Accession M19729). Lower panel: The sequence of the chimeric $h\beta_2m/\zeta$ gene (SEQ ID NO:3), joined via the XhoI site, in clone 21-2 (Example 2). Restriction sites used for cloning are underlined: tctaga- XbaI; ctcgag- XhoI; gaattc- EcoRI. atg initiation codons, taa stop codons and the HLA-A2 bridge coding sequence are shaded.

FIGS. 6A-6B show components for the preparation of a chimeric antigenic peptide/$h\beta_2m/\zeta$ construct and a representation thereof. FIG. 6A shows transformation of a native class I MHC molecule (left) into a chimeric molecule with a ζ chain via a bridge peptide (middle) and to a further chimeric molecule in which an antigenic peptide is linked to the N-terminus of the chimeric $h\beta_2m/\zeta$ molecule (right). FIG. 6B depicts a chimeric antigenic peptide/$h\beta_2m/\zeta$ construct designed to load antigenic peptides onto the construct of FIG. 6A. pr—the SRα promoter; lead—leader peptide of $h\beta_2m$; p—antigenic peptide; li—peptide linker; br—HLA-A2 peptide bridge; tm+cyt —transmembranal and cytosplasmic domains. The construct was cloned downstream of SRα promoter of the pBJ1-Neo expression vector. Numbers and directions of PCR primers used for cloning are indicated. Primers 6086, 6087 and 6338 are specific to the NP, Ha and IB peptides, respectively. (Example 4).

FIG. 7 shows the DNA sequences encoding the three chimeric antigenic peptide/$h\beta_2m/\zeta$ polypeptides described in Example 4. Upper panel: DNA sequence of the coding region of the chimeric nucleoprotein (NP) peptide/$h\beta_2m/\zeta$ gene (SEQ ID NO:4) from clone 406-20. Middle panel: The part of the coding region of the chimeric hemagglutinin (Ha) peptide/$h\beta_2m/\zeta$ gene (SEQ ID NO:5) in clone 407-4, from its 5' end till the BamHI site in the peptide linker-encoding segment. From this site till its 3' end this gene is identical to 406-20. Lower panel: The part of the coding region of the chimeric insulin B chain (IB) peptide/$h\beta_2m/\zeta$ gene (SEQ ID NO:6) in clone 408-9, from its 5' end till the BamHI site in the peptide linker-encoding segment. From this site till its 3' end this gene is identical to 406-20. All sequences are identical to that of clone 21-2 (see FIG. 3) starting 24 nucleotides downstream of the underlined BamHI site. Restriction sites used for cloning are underlined: tctaga- XbaI; ggattc- BamHI; ctcgag XhoI; gaattc- EcoRI. atg initiation codons, taa stop codons, the HLA-A2 bridge and the three antigenic peptide coding sequences are shaded.

FIGS. 10A-10B show a schematic representation of the chimeric $DR_\alpha/\zeta$ gene, clone 23-2 (Example 7), wherein numbers and directions of PCR primers used for cloning are indicated, and the DNA sequence of the chimeric $DR_\alpha/\zeta$ gene 23-2 and its separate components, respectively. In FIG. 10B: Upper panel—DNA sequence of the coding region of the human HLA-DR$_\alpha$(SEQ ID NO:7) (DRA*0101 gene in GenBank Accession J00194). Lower panel: DNA sequence of the chimeric $DR_\alpha/\zeta$ gene (SEQ ID NO:8), joined via the XbaI site. Restriction sites used for cloning are underlined: ctcgag- XhoI; tctaga- XbaI; gaattc- EcoRI. atg initiation codons, taa stop codons and the one junctional nucleotide from each of the two genes are shaded.

DETAILED DESCRIPTION OF THE INVENTION

Figure 1:
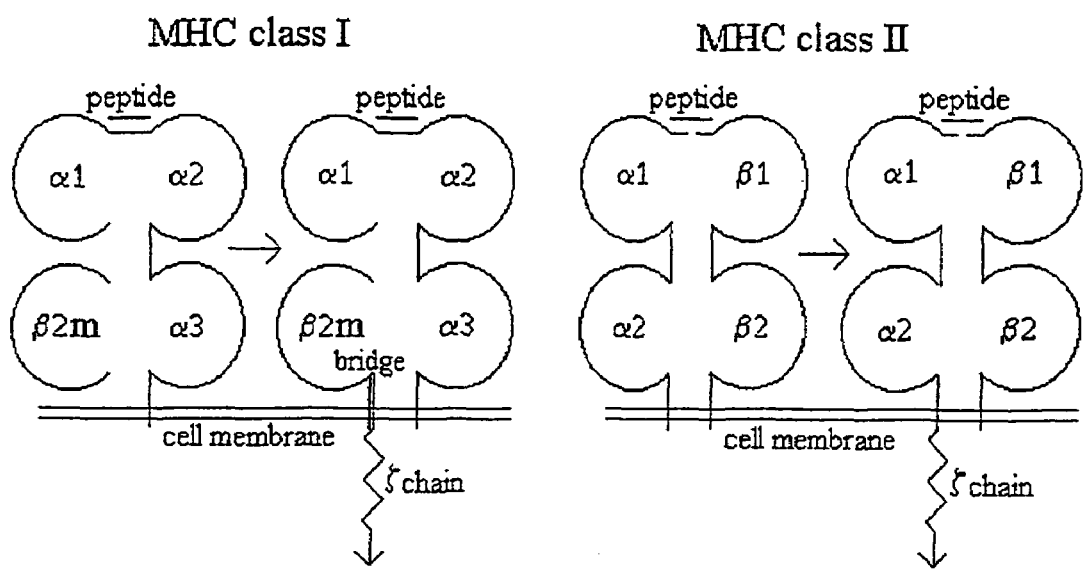
FIG. 1 shows schematic drawings of native class I and class II MHC molecules and of chimeric MHC molecules linked to a zeta (ζ) polypeptide according to the invention. Left panel—MHC class I., native (left) and chimeric (right). $\beta_2m$—$\beta_2$ microglobulin; α1, α2, α3—heavy chain domains; bridge—a short peptide connecting $\beta_2m$ to the cell membrane; arrow—activation signal. Right panel—MHC class II, native (left) and chimeric (right). α1, α2—α chain domains; β1, β2—β chain domains.

Specific direction of an immunointervention procedure against the pool of auto- or allo-specific T cells in autoimmune disease or in allograft rejection, respectively, demands a well-defined structural or functional common denominator which can serve as an identification tag for this pool.

The idea underlying the present invention is that the trivial common denominator of the whole panel of T cells is to recognize a given MHC::peptide ligand, irrespective of TCR gene products of these cells. The present invention provides a new mechanism devised to trigger a potent reaction against harmful T cells by following their specific interaction with the MHC::peptide ligand. This can only be achieved if the ligand is engineered to be linked to an adequate effector function, activated upon its engagement with specific TCRs.

The present invention demonstrates the feasibility of creating genetically-engineered DNA molecules encoding a chimeric polypeptide comprising a MHC component and a signal transduction element component. When introduced into cells, particularly T cells, this construct will endow the cells with the capacity to transduce-T-cell activation signal. Thus, T cells expressing these chimeric polypeptides together with relevant antigenic peptide, are rendered functional against other specific T cells which are restricted by the modified MHC products.

The present invention relates to a DNA molecule encoding a chimeric polypeptide comprising (a) a component of a MHC molecule capable of association on a cell surface with an endogenous MHC molecule component of the same class, and (b) an intracellular region of a signal transduction element capable of activating T cells.

In one preferred embodiment of the invention, the MHC component (a) is a monomorphic component such as the non-MHC encoded human $\beta_2$-microglobulin ($\beta_2$m) molecule or the α chain of a HLA-DR molecule.

In one most preferred embodiment, component (a) is monomorphic $\beta_2$m, the class I MHC light chain, which is capable of association on a cell surface with an endogenous class I heavy chain HLA molecule. The $\beta_2$m molecule is linked to component (b) by a bridge peptide having about 10-15 amino acid residues. Preferably, this bridge peptide has a sequence comprised within the membrane-proximal sequence of a class I heavy chain HLA molecule. In a preferred embodiment, this bridge peptide has 13 amino acid residues comprised within the extracellular membrane-proximal sequence of the class I heavy chain HLA-A2 molecule, and has the sequence: Leu Arg Trp Glu Pro Ser Ser Gln Pro Thr Ile Pro Ile (SEQ ID NO:9)

In another preferred embodiment, component (a) is the monomorphic HLA-DRα chain, which is capable of association on a cell surface with an endogenous HLA-DRβ chain.

In another embodiment, the MHC component (a) is a polymorphic component selected from: (i) an α chain of class I HLA-A, HLA-B or HLA-C molecule, which is capable of association on a cell surface with endogenous $\beta_2$m; (ii) an α chain of class II HLA-DP or HLA-DQ molecule, which is capable of association on a cell surface with endogenous HLA-DPβ or HLA-DQβ chain; or (iii) a polymorphic β chain of class II HLA-DP, BLA-DR or HLA-DQ molecule, which is capable of association on a cell surface with an endogenous HLA-DPα, HLA-DRα or HLA-DQα chain.

Component (b) of the chimeric activation receptor of the invention comprises the intracellular region of a suitable signal transduction element capable of activating T cells such as, but not being limited to, a component of T-cell receptor CD3 such as the zeta (ζ) or eta (η) polypeptide, a B cell receptor polypeptide or an Fc receptor polypeptide. As mentioned in the Background section hereinbefore, the cytoplasmic regions of the CD3 chains contain a motif designated the immunoreceptor tyrosine-based activation motif (ITAM), which has been shown to associate with cytoplasmic tyrosine kinases and to participate in signal transduction following TCR-mediated triggering. This motif is found in a number of other receptors including the Ig-α/Ig-β heterodimer of the B-cell receptor complex and Fc receptors for IgE and IgG, and three copies of it are found in the long cytoplasmic domains of the the ζ and η chains.

In a preferred embodiment, component (b) of the chimeric molecule comprises the transmembranal and cytoplasmic regions of the human CD3 ζ polypeptide.

In another embodiment, component (b) comprises the transmembranal and cytoplasmic regions of a B-cell receptor polypeptide such as the Ig-α or Igβ chain, the cytoplasmic tails in both being long enough to interact with intracellular signaling molecules. In a further embodiment, component (b) comprises the transmembranal and cytoplasmic regions of Fc receptor polypeptides such as FcεRI, FcγRI or FcγRIII chains. FcγRI, a high-affinity receptor expressed on the surface of mast cells and basophils, contains four polypeptide chains: an α and β chain and two identical disulfide-linked γ chains that extend a considerable distance into the cytoplasm and each has an ITAM motif FcγRI, or CD64, is the high affinity receptor for IgG, expressed mainly on macrophages, neutrophils, eosinophils and dendritic cells. It comprises an α chain and two disulfide-linked γ chains. This structure is also typical to FaγRIII, or CD16, which is the low affinity receptor for IgG, found on NK cells, eosinophils, macrophages, neutrophils and mast cells. CD3 ζ chain is found instead of the γ chain in a fraction of FcγRIII.

In an additional embodiment, the invention provides a DNA molecule encoding for a chimeric polypeptide as described above, wherein said chimeric polypeptide further comprises an antigenic peptide related to an autoimmune disease, said antigenic peptide being linked to component (a) of said chimeric polypeptide by a peptide linker. The antigenic peptide will typically have 8-10 amino acid residues when component (a) is class I $\beta_2$m or α chain, and will typically have 13-18 amino acid residues when component (a) is class II α or β chain.

The DNA molecule of the invention is constructed from components (a) and (b) under a suitable promoter by cloning in a suitable vector by DNA manipulation techniques well-known in the art. For example, cDNA segments encoding components (a) and (b) are cloned by reverse transcriptase-polymerase chain reaction (RT-PCR) using mRNA from appropriate cells, with suitable primers that contain appropriate restriction sites for insertion of the PCR products into a suitable expression vector. The resulting vector containing the DNA encoding the chimeric polypeptide is then used for transfection of the desired cells.

In another aspect, the invention relates to an expression vector comprising a DNA molecule of the invention. Any expression vector suitable for transfection or infection of mammalian cells and in which cells the vectors are capable of directing the regulated expression of cloned genes into recombinant polypeptides, can be used according to the invention. Since the invention relates to the expression of the chimeric polypeptide in human cells, these vectors are preferably viral vectors such as retroviral or adenovirus vectors.

In another aspect, the present invention provides a cell which expresses a chimeric polypeptide comprising (a) a component of a MHC molecule capable of association on a cell surface with an endogenous MHC molecule component of the same class, and (b) an intracellular region of a signal transduction element capable of activating T cells. The cells are preferably immune cells selected from T helper cells (CD4$^+$), natural killer (NK) cells and, most preferably, T cytotoxic cells (CTL, CD8$^+$), capable of recognizing and binding to harmful T cells and causing their elimination or inactivation.

Immune cells which express a chimeric polypeptide containing only components (a) and (b) without any additional peptide, are capable of binding to, and eliminating, alloreactive cells causing transplant rejection.

Immune cells which express a chimeric polypeptide containing components (a) and (b) and one or more additional peptides related to a certain autoimmune disease, will be able to bind to, and eliminate, autoreactive cells causing said autoimmune disease. For this purpose, the peptide (or peptides) can also be exogenously supplied by incubation of cells expressing a chimeric polypeptide containing only components (a) and (b) with one or more antigenic peptides or one or more proteins associated with the autoimmune disease to be treated. The peptide, or peptides, can also be processed and presented by the immune cell following the introduction into the cell of a gene encoding one peptide or a number of peptides, from the same protein or from different proteins associated with the disease.

The invention further provides a method for prevention and/or treatment of graft rejection, which comprises administering to a patient in need thereof at suitable times T cells which express a chimeric polypeptide comprising (a) a component of a MHC molecule capable of association on a cell surface with an endogenous MHC molecule component of the same class, and (b) an intracellular region of a signal transduction element capable of activating T cells. For the treatment of graft-versus-host disease (GVHD), the cells administered are autologous T cells, whereas for the treatment of host-versus-graft reaction, the cells administered are donor T cells.

The invention still further provides a method for the prevention and/or treatment of an autoimmune disease which comprises administering to a patient in need thereof autologous T cells which express a chimeric polypeptide comprising an antigenic peptide related to said autoimmune disease linked by a peptide linker to a component of a MHC molecule capable of association on a cell surface with an endogenous MHC molecule component of the same class, followed by an intracellular region of a signal transduction element capable of activating T cells.

The invention yet further provides a method for the prevention and/or treatment of an autoimmune disease which comprises administering to a patient in need thereof autologous T cells which express a chimeric polypeptide comprising (a) a component of a MHC molecule capable of association on a cell surface with an endogenous MHC molecule component of the same class, and (b) an intracellular region of a signal transduction element capable of activating T cells, and wherein one or more antigenic peptides or proteins related to said autoimmune disease are exogenously loaded in the groove of the MHC complex formed by the association of component (a) with the endogenous MHC molecule component, or processed and presented by the MHC complex following internalization of exogenous polypeptides or expression of an introduced gene encoding the antigenic peptide or protein.

The working hypothesis underlying this invention is that once MHC components expressed in T cells (=effector cells) are supplemented with T cell signaling domains from T-cell activation molecules such as the CD3 $\zeta$ and $\eta$ chains, these chimeric MHC-signal transduction element molecule will be capable of triggering T-cell activation upon encountering specific TCRs on other T cells (=target cells). On the surface of the effector T cell, these chimeric MHC components are expected to pair with their complementary, native MHC products and allow normal antigen presentation.

The MHC components in these chimeric polypeptides can either be monomorphic such as $\beta_2$m (for class I) or HLA-DR$\alpha$ (for class II), or polymorphic, such as all class I heavy $\alpha$ chains and other HLA class II $\alpha$ or $\beta$ chains. The signal transducing element of the chimeric polypeptide can be, for example, the $\zeta$ chain of the CD3 complex or the $\gamma$ chain of an Ig Fc receptor complex. When the effector cell is a CTL, activation is expected to lead to target T cell lysis via Fas signaling or cytotoxin release.

This concept lays the grounds for a novel immunotherapeutic approach designed to direct genetically-modified CTL against harmful T cells, resulting in specific elimination or inactivation of the latter. This approach may be applicable to transplantation and autoimmune diseases (and to other disorders, such as allergy or asthma), targeting only specific alloreactive or autoreactive CD4$^+$ and CD8$^+$ T cells, respectively.

A special characteristic of the invention is its universality when monomorphic MHC components are employed, meaning that the chimeric genes can be applied in a universal manner, namely, irrespective of HLA alleles.

In transplantation protocols, donor CTL will be transduced ex-vivo with the DNA molecule encoding the chimeric MHC polypeptide, selected for expression of the introduced gene, expanded through continuous activation and administered to the recipient in proper timing and amount during the transplantation procedure. In the class I situation, these cells will be able to -lyse allospecific recipient CTL, with potential coverage of the entire HLA class I allelic spectrum due to $\beta_2$m monomorphism. Since alloreactivity is often not peptide-specific, the majority of recipient alloreactive cells will become targets. Recipient CTL specific to peptides presented by the graft but not by donor CTL are expected to escape recognition, but are likely to constitute only a minor fraction of the alloreactive cell population. Activated human T cells, including CD8$^+$ cells, express class II molecule and can function as professional antigen presenting cells (Barnaba, et al., 1994) Chimeric HLA class II-transduced, activated donor CTL should therefore recognize allospecific recipient CD4+ cells. A recent report of a clinical trial (Bonini, et al., 1997) demonstrates that genetically modified donor T cells can indeed function in the recipient. Suicide gene-mediated elimination of such cells following allogeneic BM transplantation could control host-versus-graft reaction in leukemic patients.

For (GVHD prevention, recipient T cells isolated and propagated prior to treatment, can be similarly transduced ex-vivo with chimeric class I and class II genes. Following their re-infusion into the patient, these cells are expected to act specifically against recipient anti-donor T cells.

In autoimmune diseases associated, for example, with HLA-DR, patient's CD8+ T cells are transduced ex-vivo with a chimeric DRα gene, selected, activated and cultured with the autoantigen proteins or peptides. Upon re-infusion into the patient, these cells are expected to act specifically against DR-restricted autoreactive cells.

Another possible result of the therapeutic protocols suggested herein is the triggering of an anti-TCR immune response, similar in essence to those obtained following vaccination with TCR peptides or with whole autoreactive T cells (Howell, et al., 1989;Vandenbark, et al., 1991), and directed specifically against the pathogenic cells. Such an outcome may be mediated through local cytokine release by the engineered effector T cells.

In addition to CTL lytic machinery, genetic coupling of MHC chimeras to other effector functions in either CD4+ or CD8+ cells, can be pursued. For example, in MS, it may be favorable to instruct them to mediate secretion of cytokines which suppress inflammatory T cells, such as TGF-β, upon specific interaction with their target T cells.

The invention will now be illustrated by the following non-limiting Examples.

EXAMPLES

Materials and Methods

Materials: Monoclonal antibodies (mAbs) to mouse H-2K$^k$ and H-2K$^d$ were purchased from PharMingen (San Diego, Calif., USA). Another mAb to mouse H-2 K$^k$ (from rat) was purchased from Zymed (San Francisco, Calif., USA). MAb against human β$_2$m, polyclonal goat anti-mouse IgG (FAB specific)-FITC conjugated, puromycin, β-Galactosidase, methyl tetrazolium (MTT) and concanavalin A (ConA) were all purchased from Sigma (St Louis, Mo., USA). G418 Sulphate was from Life Technologies (Glasgow, UK).

Cell lines: MD45 is a CTL hybridoma of BALB/c mice, allospecific to H-2b (Kaufmann et al., 1981). Cells were cultured in DMEM, supplemented with 10% heat-inactivated fetal calf serum (HI-FCS), 2 mM L-Glutamine, 1 mM sodium pyruvate, Pen-Strep Solution (penicillin 10,000 units/ml, streptomycin, 10 mg/ml at 1:1000 dilution), all from Biological Industries (Beit Haemek, Israel). HK9.5-24 and HK-8.3-5H3 are CTL hybridomas of BALB/1 origin (Stryhn et al., 1994). Cells were cultured in RPMI 1640 (Biological Industries, Beit Haemek, Israel) supplemented with 10% HI-FCS, 2 mM L-glutamine, 50 μM β-mercaptoethanol (β-ME), 10 mM HEPES buffer and Pen-Strep Solution at 1:1000 dilution. CTL-L cell line was cultured in RPMI 1640 medium supplemented with 5% HI-FCS, 10 mM Hepes, 50 μM β-ME, 2 mM L-glutamine, Pen-Strep solution at 1:1000 dilution supplemented with 5% TCGF (from rat serum following polyclonal T cell activation).

DNA transfection: An 0.8 ml of 1.5×10$^6$ cell/ml (MD45 or subsequent clones) were mixed in 4 mm sterile electroporation cuvette (ECU-104, EquiBio, Ashford, UK) with 10 μg DNA of the constructed plasmid and 5 μg DNA of the selection plasmid and placed on ice. Transfection was performed by electroporation using Easyject Plus electroporation unit (EquiBio, Ashford, UK) at 350V, 750 μF. Cells were resuspended in fresh medium and cultured for 24-48 hours in 96-well plates prior to addition of the selecting drug (2 mg/ml G418 or 1 μg/ml puromycin). Resistant clones were first expanded in 24-well plates.

FACS analysis: 10$^6$ cells were washed with phosphate-buffered saline (PBS) containing 0.02% sodium azide and incubated for 30 minutes on ice with 100 μl of the anti-human β$_2$m mAb (Sigma) at 10 μg/ml or the same concentration of a control antibody. Cells were then washed and incubated on ice with 100 μl of 1:100 dilution of goat anti-mouse IgG (FAB specific)-FITC conjugated polyclonal antibody (Sigma) for 30 minutes. Cells were washed and resuspended in PBS and analyzed by a Flow Cytometer (Becton Dickinson).

Cell stimulation assay: Cells at 5×10$^5$ cells/ml were incubated overnight in 24-well plates in the presence of Con A (usually at 10 μg/ml), anti-mouse K$^k$ or K$^d$ mAb (usually at 5 μg/ml, immobilized overnight and washed 3 times in PBS) or with target cells at 5×10$^5$ cells/ml. Total volume was 1 ml.

β-Galactosidase enzymatic assay: 20-24 hours post-stimulation, cells were harvested in 1.5 ml Eppendorf tubes and centrifuged at 7000 rpm for 2 min at room temperature. Supernatant was collected for an IL-2 production assay. The pellet was washed 3 times in fresh PBS and assayed for β-galactosidase (β-Gal) using β-Galactosidase Enzyme Assay System Kit (Promega, Wis., USA) according to the manufacturer's instructions. The assay was developed in 96-well plates and was read with SLT Spectra ELISA Reader (SLT-Labinstruments GmbH, Salzburg, Austria) at 415 nm. Standard curve was produced with commercial β-Gal (Sigma).

IL-2 production assay: IL-2 was assayed according to the established bioassay procedure (Mosmann, 1983). CTL-L cells were washed 3 times in medium and resuspended at 2×10$^5$ cells/ml. 50 μl of cells were placed in a well of a 96-well plate in the presence of 50 μl of the supernatant to be assayed. Following 20 hours incubation, 10 μl of 5 mg/ml MTT (Sigma) was added and the plates were incubated for additional 4 hours. 100 μl of isopropanol containing 0.04 N HCl was added, and the reactions were thoroughly mixed. Plates were read at 570 nm with 620 nm as reference in SLT Spectra ELISA Reader.

Example 1

Design of an MHC Class I Model System

In order to examine the feasibility of the conception of the invention, a class I MHC murine model system was mounted according to the general scheme presented in FIG. 1. As the MHC component, monomorphic human β$_2$m was chosen. It associates with all class I heavy chains, thus allowing universality of use, both experimentally and therapeutically. As the signaling domain, the transmembranal and cytoplasmic portions of the mouse CD3 ζ chain was chosen.

As the effector cells we used MD45 cells, a CD8$^-$ H-2$^b$-alloreactive H-2$^{d/k}$ mouse CTL hybridoma (Kaufmann, et al., 1981). These cells grow readily in culture, are highly transfectable and secrete considerable amount of cytokines following activation. Their lytic capacity is, however, partially compromised, compared with primary CTLs. It was chosen to work with human rather than mouse β$_2$m in these cells, as it provides a distinct marker for the product of the chimeric gene. Human β₂m is known to pair efficiently with most mouse class I heavy chains, and it does so especially well with the K$^k$ molecule (Schmidt et al., 1981). To assure optimal interactions between the signaling domains and downstream membranal and cytoplasmic components of mouse origin involved in the signal transduction pathway, it was chosen to use mouse rather than human ζ chain.

For assessment of peptide-specific responses, which are relevant to autoimmunity, it was chosen to express the antigenic peptides linked to the amino terminus of the chimeric P₂m molecule via a flexible peptide linker. This mode of expression allows the generation of stably transfected hybridoma cells which constitutively present the antigenic peptides on their class I molecules.

Example 2

Class I MHC Construct Containing hβ₂m

Human β₂m (hβ₂m) cDNA was cloned by RT-PCR, using mRNA prepared from Jurkat (human T cell leukemia) cells, with the following primers:

```
1st strand primer, 4337, containing an XhoI restriction site:
5' G CTG GCT CGA GGG CTC CCA TCT CAG CAT GTC TCG ATC CCA CTT 3' (SEQ ID NO:10)

2nd strand primer, 30287, containing an XbaI site:
5' GGG TCT AGA GCC GAG ATG TCT CGC TCC GTG 3'                     (SEQ ID NO:11)
```

A cDNA segment encoding the transmembranal and cytoplasmic regions of the murine CD3 ζ chain was cloned by RT-PCR from mRNA of MD45 cells with the following primers:

```
1st strand primer, 27246, containing an EcoRI site:
5' GCG GAA TTC TTA GCG AGG GGC CAG GGT 3'                          (SEQ ID NO:12)

2nd strand primer, 4840, containing an XhoI site:
5' GAG CCC TCG AGC CAG CCC ACC ATC CCC ATC CTC TGC TAC TTG CTA GAT 3' (SEQ ID NO:13)
```

Figure 2:
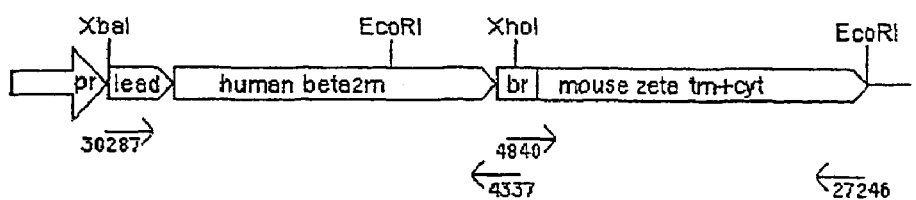
FIG. 2 depicts a chimeric human $\beta_2m/\zeta$ genetic construct of the invention cloned downstream of SRα promoter of the pBJ1-Neo expression vector. pr—promoter; lead—leader peptide of human $\beta_2m$; br—HLA-A2-derived peptide bridge; tm+cyt—transmembrane and cytoplasmic domains of CD3 ζ. Numbers and directions of PCR primers used for cloning are indicated.

While associated with the class I heavy chain HLA-A2, the distance of the C terminus of hβ₂m from the cell membrane is equivalent to that occupied by the 13 membrane-proximal amino acids (Bjorkman, et al., 1987) of the heavy chain. In an attempt to preserve class I spatial organization, this HLA-A2-derived 13-amino acid stretch was chosen to link hβ₂m to the membrane. This sequence has been incorporated into the cloned genes via the PCR primers 4337 and 4840. The restriction sites included in the PCR products have been used for a single step insertion of both products into the pBJ1-Neo expression vector (Lin et al., 1990), cleaved with XbaI+EcoRI, to produce clone 21-2. The resulting chimeric gene codes for hβ₂m, bridged to the cell and equipped with 4 chain signal transduction domains, as illustrated in FIG. 2.

The assembled gene comprises the following DNA stretches:
1. hβ₂m GenBank Accession (G.B.A.) AF072097, positions 801-1157
2. HLA-A2 G.B.A. K02883: 2380-2389+2489-2517. This sequence is CTG AGA TGG GAG CCG TCT TCC CAG CCC ACC ATC CCC ATC SEQ ID NO:14) and it encodes the 13-amino acid peptide: Leu Arg Trp Glu Pro Ser Ser Gin Pro Thr Tie Pro Ile (SEQ ID NO:9). The original Pro-Ser-Ser coding stretch was converted into CCC TCG AGC, encoding the same amino acids, so as to create an XhoI cloning site (CTCGAG).
3. Mouse CD3 ζ transmembrane (tm)+cytoplasmic (cyt) G.B.A. M19729: 193-597. The corresponding sequence in the human ζ tm+cyt is G.B.A. J04132: 165-566.

The complete nucleotide sequence assembled coding region and its human β₂m and mouse CD3 ζ chain gene constituents are presented ini FIG. 3.

Figure 4:
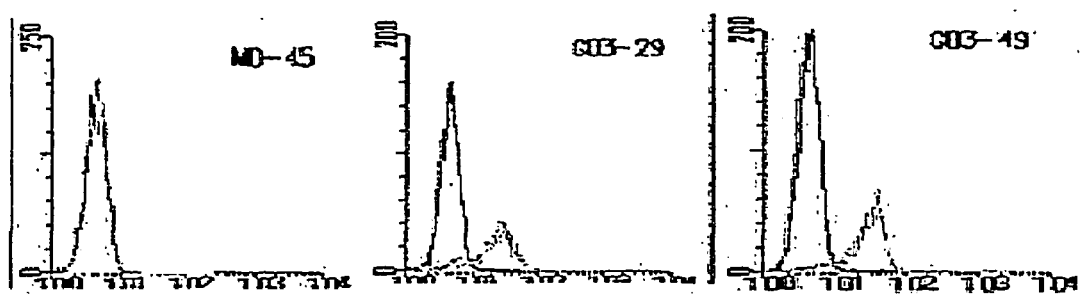
FIG. 4 shows flow cytometry analysis of surface expression of $h\beta_2m$ on MD45 hybridoma parental cells and two $h\beta_2m/\zeta$ transfectants, 29 and 49 (Example 2). Pale line—staining with an anti-h$\beta$2m mAb. Dark line—control staining with an irrelevant antibody.
Figure 5:
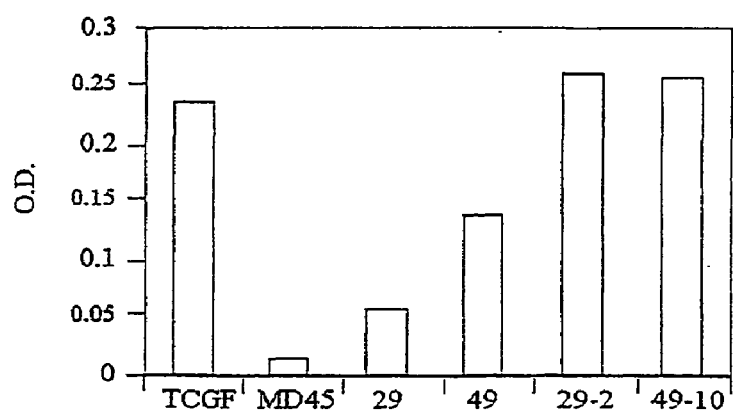
FIG. 5 shows IL-2 production after stimulation of chimeric $h\beta_2m/\zeta$ transfectants with an immobilized anti-H-2K$^k$ mAb. IL-2 was monitored with a CTL-L bioassay, which was developed via an MTT colorimetric assay (see "Materials and Methods"). MD45—parental hybridoma cells; 29 and 49—primary transfectants; 29-2 and 49-10—respective sub-clones. TCGF control reflects maximal CTL-L growth.

This DNA construct was transfected into MD45 cells. G418-resistant clones were subjected to FACS analysis, using an anti-hβ₂m mAb (Sigma M7398, St Louis, Mo., USA), in order to evaluate cell surface expression of the chimeric polypeptide. Approximately 50% of the clones were intensively stained. Staining of representative clones 29 and 49 are shown in FIG. 4. To test whether the chimeric β₂m creates functional MHC complexes on the cell surface, plastic wells were coated with a rat anti-mouse anti-H-2K$^k$ mAb (Zymed 24-1400, San Francisco, Calif., USA)), and transfectants were assayed for their ability to secrete interleukin 2 (IL-2) following incubation with the immobilized antibody. Indeed, 2 of the clones tested, 29 and 49, secreted significant amount of the lymphokine to the medium, as monitored by a CTL-L bioassay. These have been subcloned (clones 29-2 and 49-10) and a high level of secretion was now evident, as shown in FIG. 5. These results demonstrate both functional association of the chimeric hβ₂m with the K$^k$ heavy chain and coupling of these engineered class I molecule to the T-cell activation pathway.

Example 3

Construction of a Reporter System

Specific interactions between engineered effector cells and target T cells is expected to result in cytokine release by both parties. If both are of mouse origin, the source of the detected cytokines will be ambiguous. It was chosen to tackle this problem by co-transfecting the MD45 cells with plasmid 21-2 obtained in Example 2 above and with a genetic construct encoding the lacZ reporter gene driven by the minimal promoter of the human IL-2 gene [NF-AT-LacZ, kindly provided by Dr. N. Shastri, University of California (Karttunen et al., 1991)]. This was transfection 412. In addition, MD45 cells were co-transfected with the NF-AT-lacZ reporter gene and the pBJ1-Neo vector (transfection 392). For preliminary screening, G418-resistant clones were incubated with the T-cell mitogen Con A, and IL-2 gene activation was evaluated by the colorimetric ONPG assay, which monitors β-Gal activity. ONPG detection assay was again used with the strongest clones from each transfection incubated with: 1) Con A; 2) an anti-H-2K$^k$ mAb (Pharmingen A6051D); 3) no stimulation. Results of clones and MD45 parental cells are presented in Table 1. These results indicate that that the reporter gene is functional in the transfected cells and that the chimeric $\beta_2$m molecule recruits NF-AT, the T-cell specific nuclear factor, as a downstream transcription factor in the TCR-mediated signaling pathway. Clones 412-19 and 392-14 were further subcloned, giving rise to clones 412-19-1-6 and 392-14-1, respectively.

β-Gal enzymatic assay was carried out with MN45 parental hybridoma cells, a transfectant expressing both the chimeric h$\beta$2m/ζ construct and the NF-AT-LacZ reporter gene (412-19) and another transfectant (392-14), expressing only the reporter gene, were assayed. Results from a representative experiment are presented in Table 1 as OD$_{405}$ of a calorimetric Lac-Z assay.

In addition, we chose to study the insulin B chain (IB) peptide, associated with K$^d$. This setting is relevant to the diabetes animal model in NOD mice, and is designed to be tested with the K$^d$-restricted, diabetogenic CD8$^+$ clone G9C8, specific to this peptide (Wong, et al., 1999).

In order to obtain high density of peptides NP50-57 and Ha255-26 and the peptide from insulin B chain (IB) on the effector T cells of the present invention, three genetic constructs were assembled designed to link those peptides to the amino terminus of h$\beta_2$m covalently via a flexible peptide linker (see FIG. 6A). This configuration has been recently shown to create functional CTL targets with H-2 D$^b$, K$^d$ and D$^d$ (Uger et al., 1998; Uger et al., 1999; White et al., 1999). The genetic design of these constructs is schematically delineated in FIG. 6B. The linker peptide chosen for this purpose was the one used by White et al., 1999, namely, a 13-amino acid peptide of the sequence:

```
Gly-Gly-Gly-Gly-Ser-Gly-Gly-Gly-Ser Gly-Gly-Gly-Ser,    (SEQ ID NO:15)
encoded by:

GGA GGT GGC GGG TCC GGA GGT GGT TCT GGT GGA GGT TCG.    (SEQ ID NO:16)
```

We have changed the last G in the 4th Gly to an A, thus creating a unique BamHI site (GGATCC), which was useful in the cloning procedure.

TABLE 1

| Clone | Con A | Anti-H-2 K$^k$ | No Stim. |
|---|---|---|---|
| 412-19 | 0.074 | 0.160 | 0.002 |
| 392-14 | 0.395 | 0.007 | 0.011 |
| MD45 | | 0.001 | |

Example 4

Assembling Genetic Constructs for Testing Peptide Specificity

In order to target alloreactive T cells, the chimeric $\beta_2$m/ζ chain construct may be sufficient. However, since autoreactive T cells usually recognize a specific self-peptide in the context of MHC, it was important to demonstrate that the 4a. Genetic Construct Containing the Peptide NP50-57

The 5' primer of the upstream fragment was 30287 (see Example 2 above) and was the same for all 3 peptides, corresponding to the 5' end of h$\beta_2$m leader peptide, and harboring an XbaI site. The original NP50-57 amino acid sequence is:

Ser Asp Tyr Glu Gly Arg Leu Ile (SEQ ID NO:17).

The NP nucleotide sequence of A/Japan/305/57 could not be found in the gene bank, and the nucleotide sequence was derived from a related strain, H3N2 A/Akita/1/94, G.B.A. U71144: 148-171: AGT GAT TAT GAA GGG CGG TTG ATC (SEQ ID NO:18).

The 3' primer was 6086, containing a BamHI restriction site:

```
5' CGC GGA TCC GCC ACC TCC GAT CAA CCG CCC TTC ATA ATC ACT AGC CTC AAG GCC AGA AAG 3'  (SEQ ID NO:19)
``` effector cells can respond to K$^k$-restricted CD8$^+$ T cells specific to a given peptide, if the latter is presented by the transfectants' K$^k$. To perform experiments along this line we exploited two existing K$^k$-restricted murine CD8$^+$ T cell hybridomas [kindly provided by Dr. A. Stryhn, University of Copenhagen (Stryhn et al., 1994)]. One hybridoma, HK9.5-24, is specific to an influenza virus nucleoprotein (NP) peptide (NP50-57), and the other, HK8.3-5H3, is specific to an influenza virus hemagglutinin (Ha) peptide (Ha255-262). These hybridomas and peptides were only employed as a model system for peptide specificity, which provides solid internal controls, and have no biological relevance to, and are not encompassed by, the present invention.

The 2nd set of primers was designed to amplify the rest of the linker and the full, mature h$\beta_2$m with the part of the HLA-A2 bridge.

The 5' primer, 5187, was the same for the 3 peptides and contains a BamHI site:

```
5' GCG GGA TCC GGA GGT GGT TCT GGT GGA GGT TCG ATC CAG CGT ACT CCA AAG 3'  (SEQ ID NO:20)
```

The 3' primer for all peptides was 4337 (see Example 2 above) containing an XhoI site.

4b. Genetic Construct Containing the Peptide Ha 255-262

The original Ha 255-262 peptide of influenza virus strain A/Japan/305/57 has the sequence: Phe Glu Ser Thr Gly Asn Leu Ile (SEQ ID NO:21), and is encoded by G.B.A. L20407: 806-829

5' CGC GGA TCC GCC ACC TCC AAT TAG ATT ACC AGT ACT CTC AAA AGC CTC AAG GCC AGA AAG 3' (SEQ ID NO:23)

4c. Genetic construct containing the IB peptide

The peptide sequence is Leu Tyr Leu Val Cys Gly Glu Arg Gly (SEQ ID NO:24), and it is derived from mouse preproinsulin: G.B.A. X04725: 943-969.

5' CGC GGA TCC GCC ACC TCC GCC ACG CTC CCC ACA CAC CAG GTA GAG AGC CTC AAG GCC AGA AAG 3' (SEQ ID NO:26)

The 3 final constructs were assembled in one cloning step. The XbaI/BamHI fragment for each of the 3 peptides (following subcloning and nucleotide sequence determination) was joined with the BamHI/XhoI fragment (the same one for all peptides—also subcloned and sequenced) and with the Xho/EcoRI fragment from clone 21-2, to the pBJ1-Neo vector cleaved with XbaI+EcoRI. The resulting clones were 406-20 for the NP peptide, 407-4 for the Ha peptide and 408-9 for the IB peptide. The DNA sequence of their coding stretches is presented in FIG. 7.

Example 5

Analysis of the Expression of the Chimeric $\beta_2$m with Peptides

The three plasmids of Examples 4a, 4b and 4c above were each co-transfected into MD45 cells together with the NF-AT-lacZ reporter gene. Clones generated with plasmid 406-20 were designated 797, those generated with plasmid 407-4 were designated 798, and plasmid 408-9 yielded clones 799. Twenty four G418 resistant clones from each transfection were tested for IL-2 secretion following incubation with immobilized anti-H-2K$^k$ mAb for NP and Ha peptides or anti-H-2K$^d$ mAb (Pharmingen 06091D) for the insulin peptide. Stimulation was monitored by an IL-2 bioassay, using the IL-2-dependent CTL-L cell line. IL-2 production was assayed after stimulation of MD45 cells transfected with chimeric antigenic peptide/h$\beta_2$m/$\zeta$ genes by an immobilized anti-H-2K$^k$ or anti-H-2K$^d$ mAb. IL-2 was monitored with a CTL-L bioassay, which was developed via an M4TT calorimetric assay (see "Materials and Methods"). MD45 cells serve as a negative control. Results are shown in Table 2. 797, 798, 799—are transfectants with NP-, Ha- and IB-encoding chimeric genes, respectively; clone 412-412-19-1-6, serves as a positive control;*-medium response;**-strong response.

TABLE 2

| Clone | O.D. 797 (anti-K$^k$): | Clone | O.D. 798 (anti-K$^k$): | Clone | O.D. 799 (anti-K$^k$): |
|---|---|---|---|---|---|
| 1 | 0.007 | 1 | 0.011 | 1 | 0.006 |
| 2 | 0.003 | 2 | 0.078* | 2 | 0.002 |
| 3 | 0.162** | 3 | 0.013 | 3 | 0.012 |
| 4 | 0.003 | 4 | 0.009 | 4 | 0.143** |
| 5 | 0.001 | 5 | 0.008 | 5 | 0.159** |
| 6 | 0.002 | 6 | 0.007 | 6 | 0.005 |
| 7 | 0.007 | 7 | 0.011 | 7 | 0.005 |
| 8 | 0.004 | 8 | 0.008 | 8 | 0.166** |
| 9 | 0.024* | 9 | 0.048* | 9 | 0.007 |
| 10 | 0.161** | 10 | 0.008 | 10 | 0.158** |
| 11 | 0.008 | 11 | 0.005 | 11 | 0.026* |

TABLE 2-continued

| Clone | O.D. 797 (anti-K$^k$): | Clone | O.D. 798 (anti-K$^k$): | Clone | O.D. 799 (anti-K$^k$): |
|---|---|---|---|---|---|
| 12 | 0.005 | 12 | 0.006 | 12 | 0.026* |
| 13 | 0.008 | 13 | 0.011 | 13 | 0.022* |
|  |  | 14 | 0.007 | 14 | 0.031* |
| 15 | 0.010 | 15 | 0.009 | 15 | 0.149** |
| 16 | 0.039* | 16 | 0.069* | 16 | 0.029* |
| 17 | 0.004 | 17 | 0.019 | 17 | 0.100** |
| 18 | 0.113** | 18 | 0.082* | 18 | 0.091* |
| 19 | 0.006 | 19 | 0.052* | 19 | 0.055* |
| 20 | 0.020* | 20 | 0.006 | 20 | 0.013 |
| 21 | 0.011 | 21 | 0.120** | 21 | 0.154* |
| 22 | 0.020* | 22 | 0.010 | 22 | 0.012 |
| 23 | 0.008 | 23 | 0.000 | 23 | 0.008 |
| 24 | 0.050* |  |  | 24 | 0.006 |
| MD45 | 0.003 |  |  | MD45 | 0.004 |
| 412 | 0.171** |  |  | 412 | 0.161** |

These results lend further support to our previous findings that the chimeric $\beta_2$m functionally associates on the cell surface with endogenous class I H chains, and adds H-2K$^d$ to H-2K$^k$ as molecules which are capable of transducing T cell activation signals. Unfortunately, none of the transfected clones which produced high level of IL-2 in response to the immobilized mAbs showed significant $\beta$-Gal activity following stimulation.

We decided to proceed by following a step-wise transfection protocol. This time, MD45 cells were transfected only with the chimeric gene. Cells transfected with plasmid 406-20 encoding the NP peptide generated series 419 of clones. Similarly, MD45 transfected with plasmid 407-4 encoding the Ha peptide resulted in clones denoted 420. In both cases selection was carried out with G418.

Table 3 summarizes the results of an IL-2 bioassay of a screening experiment of these two series of clones, showing all clones which elicited significant IL-2 production above background with any of the two K$^k$-restricted CTL hybridomas described above—hybridoma HK9.5-24 specific to NP50-57 and hybridoma K8.3-5H3 specific to Ha255-262. All clones were incubated in this experiment simultaneously with the two hybridomas in exactly the same conditions, as described in "Materials and Methods". This setting allows cross-reference of the tested clones, thus constituting a reliable internal control.

IL-2 production was assayed after co-incubation of clones transfected with the NP-encoding chimeric gene (419 series) or with the Ha-encoding gene (420), with the two target cells. IL-2 was monitored with the CTL-L bioassay. Only transfected cells which induced significant IL-2 production have been included. Note that under this experimental setting it is impossible to identify the source of the secreted lymphokine.

TABLE 3

|  | Clone | HK8.3-5H3 (Ha) | HK9.5-24 (NP) |
|---|---|---|---|
| NP: | 419-6 | 0.030 | 0.068 |
|  | 419-17 | 0.007 | 0.101 |
|  | 419-19 | 0.013 | 0.058 |
|  | 419-21 | 0.015 | 0.032 |
|  | 419-27 | 0.007 | 0.036 |
|  | 419-28 | 0.011 | 0.029 |
|  | 419-40 | 0.023 | 0.105 |
|  | 419-49 | 0.019 | 0.045 |
|  | 419-55 | 0.006 | 0.050 |
|  | 419-60 | 0.019 | 0.060 |
|  | 419-61 | 0.053 | 0.121 |
|  | 419-65 | 0.011 | 0.062 |
|  | Average | 0.018 | 0.064 |
| Ha: | 420-11 | 0.053 | 0.012 |
|  | 420-27 | 0.031 | 0.018 |
|  | 420-31 | 0.030 | 0.014 |
|  | 420-35 | 0.038 | 0.016 |
|  | 420-40 | 0.037 | 0.011 |
|  | 420-44 | 0.029 | 0.016 |
|  | 420-52 | 0.039 | 0.016 |
|  | 420-58 | 0.040 | 0.012 |
|  | 420-62 | 0.036 | 0.012 |
|  | 420-66 | 0.053 | 0.019 |
|  | 420-71 | 0.025 | 0.007 |
|  | Average | 0.037 | 0.014 |

This experiment indicates that co-incubation of MD45 transfectants containing a construct according to the invention expressing the influenza NP peptide with both $K^k$-restricted CTL hybridomas, results in significantly higher IL-2 secretion with HK9.5-24. The inverse is true with cells expressing the Ha peptide, which induce much higher IL-2 production when incubated with HK8.3-5H3 cells. We were unable to detect a clone exhibiting the opposite profile of response. The results strongly indicate that the chimeric antigenic peptide-$\beta_2$m-$\zeta$ chain polypeptide is properly expressed on the cell membrane in association with $K^k$ H chain. It should be noted that these experiments are not designed to determine the source of the secreted cytokine. At this stage, however, it is clear that a peptide-specific response does indeed take place following co-incubation of our modified T cells with their target CTL hybridomas, thus, that the peptide is presented on the cell surface on $K^k$ in a constitutive manner.

Example 6

Assay of Peptide Specificity of Transfected T Cells

Figure 8:
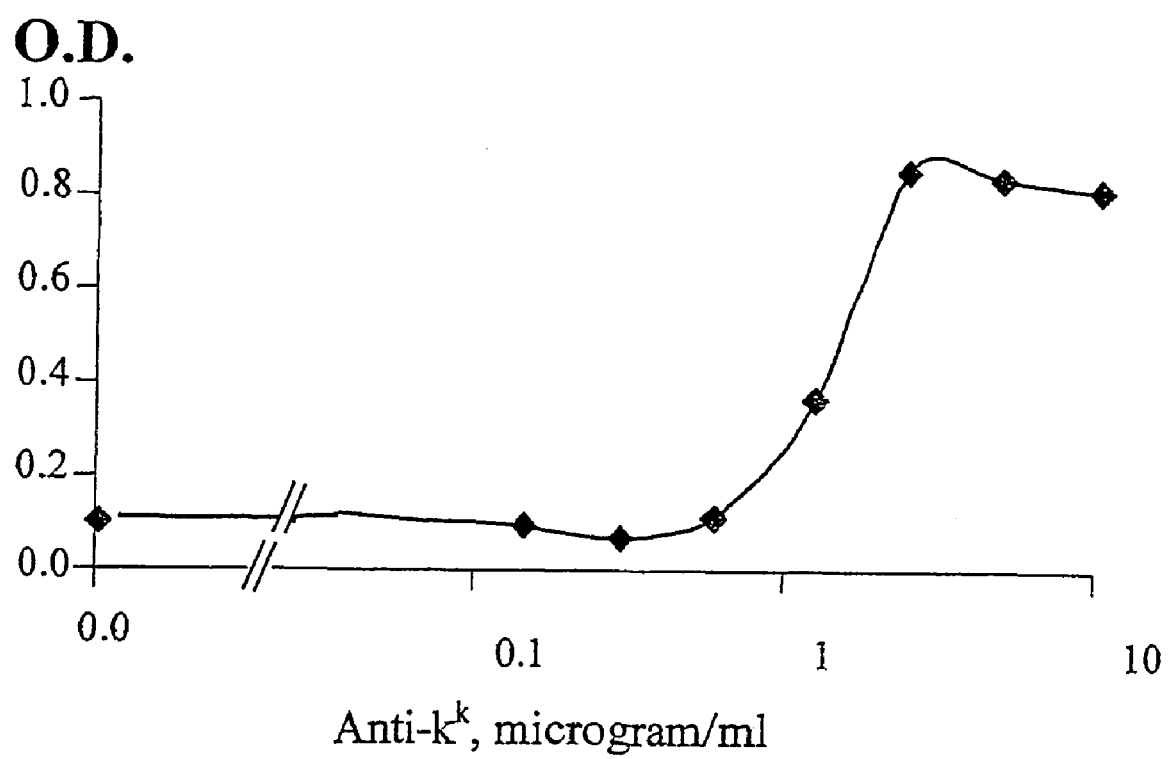
FIG. 8 is a graph showing the results of β-galactosidase (β-Gal) enzymatic assay of the dose-dependent response of clone 425-68 to serial dilutions of an immobilized anti-H-2K$^k$ mAb (Example 6). Concentrations of the mAb which was applied into the experiment well are given in the x axis on a logarithmic scale. Results are in $OD_{405}$.

As discussed above, demonstrating peptide-specific response of our clones requires unambiguous assignment of specific response to the modified MD45 effector cells, a challenge we chose to tackle by the use of the reporter gene. Implementing the approach of stepwise transfections, we chose clones 419-17 and 420-11 as the best responders, and super-transfected them with the NF-AT-LacZ reporter gene, together with an additional plasmid pMCC-ZP (kindly provided by Dr. J. Lazarowitz, Bio-Technology General, Rehovot, Israel) which allows for puromycin selection. Clones resistant to both G418 and puromycin were first tested by a β-Gal enzymatic assay for their ability to produce the enzyme in response to Con A stimulation. Cell lysates of two clones originating from 419-17, numbered 425-44 and 425-68, showed strong enzymatic activity following incubation in the presence of the Con A. One of these clones, 425-68, was then assayed for β-Gal production following stimulation by a serial dilution of the immobilized anti-$K^k$ mAb Pharmingen): A dose-dependent response was obtained and is presented in FIG. 8.

Figure 9:
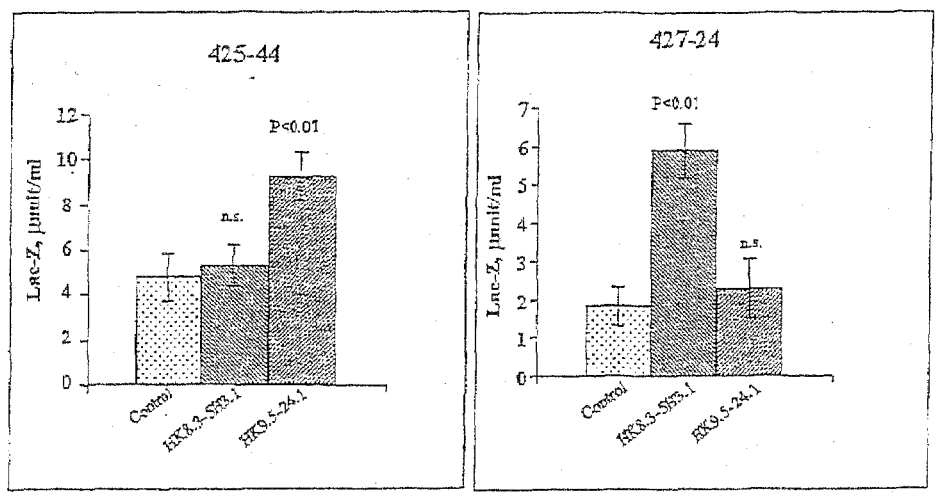
FIG. 9 shows β-Gal production by clones 425-44 (expressing NP/$h\beta_2m/\zeta$ and NF-AT-LacZ) and 427-24 (expressing Ha/$h\beta m/\zeta$ and NF-AT LacZ) after incubation with the two target cells (Example 6). The results are the summary of 15 independent experiments. Results are given in μ units of β-Gal according to a standard curve produced in each experiment with commercial β-Gal (Promega, Wis., USA). Statistical significance was assessed by ANOVA.

These two clones were then assayed (as described in "Materials and Methods") with each of the two CTL hybridomas 9.5-24 specific to NP50-57 and K8.3-5H3 specific to Ha255-26, with Con A as a positive control and with no stimulation as a negative control, monitoring basal β-Gal production by these cells. The results for clone 42544 are shown in FIG. 9. These results were typical to those obtained in similar experiments performed with the full set of two effectors and two targets, as described below, and demonstrated the expected peptide-specificity of the chimeric MHC-mediated activation.

We could not identify any strong β-Gal producers among the descendants of clone 420-11. We then decided to implement our stepwise transfection procedure in an inverted order. We started with clone 392-14-1 (see above) which expresses high level of β-Gal upon stimulation (and is G418-resistant) and introduced into these cells plasmid 407-4 (encoding the Ha peptide), together with pMCC-ZP to confer puromycin resistance. One double-resistant clone generated in this transfection, 427-24, displayed the expected phenotype. It produced β-Gal following incubation with immobilized anti-H-$2K^k$ mAb, and it led to IL-2 secretion after co-incubation with the Ha peptide-specific CTL hybridoma, HK8.3-5H3.

We then performed a series of co-incubations of our clones 425-44 and 427-24 with both target CTL hybridomas, assaying β-Gal activity, all as described in "Materials and Methods". Results are summarized in FIG. 9. Although the magnitude of the observed response in this type of assay is relatively low, its anticipated profile, namely, correlation between the antigenic peptide expressed by the responding clone and the antigenic specificity of the target CTL hybridoma, is clearly evident, as supported by the high significance value. We attribute these relatively low values to a number of factors. First, MD45 cells and their descendant clones express significantly lower levels of $K^k$, as compared to normal cells, as observed with a fluorescent microscope, using the anti-$^k$ mAb (data not shown). Second, as reported before (Stryhn et al., 1994) and confirmed by us, the hybridoma target cells do not express CD8. Third, MD45 are negative for both CD8 and CD4. These deficiencies are likely to decrease the actual number of functional interactions between the engineered MHC molecules on the effector cells and TCRs on the target cells, reduce their avidity and affect the magnitude of the transduced signal.

The results obtained above in our MSC class I model cell system demonstrates that MHC class I molecules can be converted into T cell activation receptors, and that T cells expressing these receptors can be activated in a peptide-specific manner.

Example 7

Construction of a Class II MHC Model System

Antigen presentation by class II MHC molecules on the cell surface requires a number of accessory molecules. The more important ones are a protein called invariant (Ii) chain, which acts as a chaperon for the newly synthesized class II molecules, and a class II 1HC-like molecule called HLA-DM (in humans) or H-2M (in mice), which catalyzes loading of class II molecules with endogenously-processed peptides.

These proteins are not normally expressed by cells which do not express class II, such as mouse T cells. Unlike, activated human T cells (both CD4⁺ and CD8⁺) do express surface class II HLA and are known to function as effective antigen-presenting cells (Barnaba et al., 1994).

To test chimeric HLA class II expression and its function in a human T cell system, we chose HLA-DR2, which is highly associated with MS. Several DR2 alleles have been identified, among which DR2Dw2 is the most common in DR2⁺ individuals and in most DR2⁺ MS patients (Wucherpfennig et al., 1991). Its α chain (as for all DR molecules) is encoded by the DRA*0101 gene and its β chain by DRB1*1501. The source for both these genes was an EBV-transformed human B cell line (kindly provided by Dr. D. Teitelbaum, The Weizmann Institute of Science, Rehovot, Israel). mRNA prepared from these cells served for RT-PCR amplification of the desired fragments.

7a. Assembly of DRα/Mouse ζ Chain Construct

A chimeric gene encoding the extracellular part of DRα joined to the transmembranal and cytoplasmic domains of mouse ζ chain was assembled from two components:

1. An 0.65 kb XhoI/XbaI fragment containing the 5' end of HLA-DRA*0101, including the segment encoding the leader peptide, joined to the 5' end of the stretch encoding the mouse ζ chain transmembranal domain.

The 5' primer, 32152, contains an XhoI restriction site and is specific to DRA*0101from position 11 in GenBank Accession J00194, including the ATG initiation codon. 5' GGC CCC TCG AGG CGC CCA AGA AGA AAA TGG CC 3' (SEQ ID NO:27)

The 3' primer, 3982, contains an XbaI site. It allows the in-frame joining of the 3' end of the stretch encoding the DRα extracellular portion (up to position 635 in the gene) with the 5' end of the transmembranal domain of mouse ζ (from position 193 in GenBank Accession M19729). The XbaI restriction site was introduced into the ζ chain coding sequence without changing the amino acid composition. 5' GGG TCT AGA AGG TAG CAG AGC CAC TGC TTG AGA AGA GGC 3' SEQ ID NO:28)

2. An 0.4 kb XbaI/EcoRI fragment encoding the ζ chain transmembrane and cytoplasmic domain.

The 5' primer 25528 is specific for the 5' of the ζ domain (see Example 1 above) and contains an XbaI site: 5' GGG TCT AGA TGG AAT CCT CTT CAT C 3' (SEQ ID NO:29)

The 3' primer is the primer 27246 used in Example 1 above for the assembly of the chimeric β₂m gene.

Figure 10A:
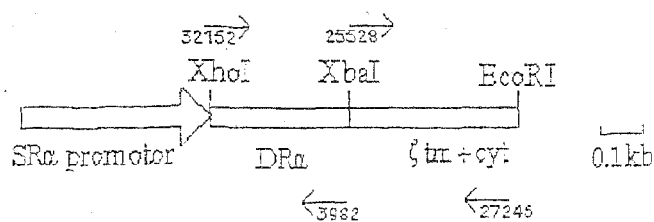

Both PCR products were cloned in a single step into the expression vector pBJ1-Neo prepared with XhoI+EcoRI, to produce clone 23-2. It is schematically presented in FIG. 10A and the complete nucleotide sequence of its coding region is shown in FIG. 10B.

7b. Cloning DRB*1501

The DRB*1501 gene encoding the DRβ chain was cloned in its native form, including the leader sequence, as a single PCR product, using the following primers:

The 5' one, 28239, harbors an XhoI site, and is specific to positions 17-34 in GenBank Accession M20430.

This PCR product was then cleaved with XhoI and HindIII (located approximately. 60 bp downstream of the gene's stop codon of the DRB1*1501 gene), and inserted into pBJ1-Neo.

The chimeric DRα/ζ and the native DRβ genes can be expressed in a suitable host cell such as, for example, in human T cells immortalized by Herpes virus saimiri [H. saimiri, reviewed by Meinl et al., 1995). This lymphotropic agent has been shown to transform human CD4⁺ and CD8⁺ T cells to continuous growth in culture for extended periods, independently of stimulation with APC and antigen. HLA-DR-restricted H. saimiri-transformed CD4⁺ T cell clones (Weber et al., 1993) can also serve as specific targets in this system. MBP-specific lymphokine secretion and cytolysis by the CD8⁺ cells can be assayed in experiments analogous to those described for the class I system. Efficient class II presentation of MBP peptides by the chimeric DR/ζ transfectants is expected following their incubation with MBP or its reelevant peptides (Barnaba, et al., 1994). Other MS- and diabetes-related autoantigens and additional HLA-DR restricting elements can be tested by the same experimental system.

References

Barnaba, V., Watts, C., de_Boer, M., Lane, P. and Lanzavecchia, A. (1994). "Professional presentation of antigen by activated human T cells." Eur J Immunol 24: 71-5.

Ben-Nun, A. and Cohen, I. R. (1981). "Vaccination against autoimmune encephalomyelitis (EAE): attenuated autoimmune T lymphocytes confer resistance to induction of active EAE but not to EAE mediated by the intact T lymphocyte line." Eur J Immunol 11: 949-52.

Bluestone, J. A., Leo, O., Epstein, S. L. and Sachs, D. H. (1986). "Idiotypic manipulation of the immune response to transplantation antigens." Immunol Rev 90: 5-27.

Bonini, C., Ferrari, G., Verzeletti, S., Servida, P., Zappone, E., Ruggieri, L., Ponzoni, M., Rossini, S., Mavilio, F., Traversari, C. and Bordignon, C. (1997). "HSV-TK gene transfer into donor lymphocytes for control of allogeneic graft-versus-leukemia." Science 276: 1719-24.

Carpenter, C. B., d_Apice, A. J. and Abbas, A. K. (1976). "The role of antibodies in the rejection and enhancement of organ allografts." Adv Immunol 22: 1-65.

Douillard, P., Cuturi, M. C., Brouard, S., Josien, R. and Soulillou, J. P. (1999). "T cell receptor repertoire usage in allotransplantation: an overview." Transplantation 68: 913-21.

Elias, D., Reshef, T., Birk, O. S., van der Zee, R., Walker, M. D. and Cohen, I. R. (1991). "Vaccination against autoimmune mouse diabetes with a T-cell epitope of the human 65-kDa heat shock protein." Proc Natl Acad Sci USA 88: 3088-91.

Eshhar, Z., Waks, T., Gross, G. and Schindler, D. G. (1993). "Specific activation and targeting of cytotoxic lymphocytes through chimeric single chains consisting of antibody-binding domains and the gamma or zeta subunits of the immunoglobulin and T-cell receptors." Proc Natl Acad Sci USA 90: 720-4.

5' CGC GCC TCG AGC CCC TGG TCC TGT CCT G 3'  (SEQ ID NO:30)

The 3' primer, 201793, is specific to the 3' end of the gene (positions 1114-1133):

5' GTA ATG TGT TTG TCA TAC AG 3'  (SEQ ID NO:31)

Faustman, D. (1995). "Strategies for circumventing transplant rejection: modification of cells, tissues and organs." Trends Biotechnol 13: 100-5.

French, M. B., Allison, J., Cram, D. S., Thomas, H. E., Dempsey-Collier, M., Silva, A., Georgiou, H. M., Kay, T. W., Harrison, L. C. and Lew, A. M. (1997). "Transgenic expression of mouse proinsulin II prevents diabetes in nonobese diabetic mice." Diabetes 46: 34-9.

Gross, G. and Eshhar, Z. (1992). "Endowing T cells with antibody specificity using chimeric T cell receptors." Faseb J 6: 3370-8.

Gross, G., Levy, S., Levy, R., Waks, T. and Eshhar, Z. (1995). "Chimaeric T-cell receptors specific to a B-lymphoma idiotype: a model for tumour immunotherapy." Biochem Soc Trans 23: 1079-82.

Gross, G., Waks, T. and Eshhar, Z. (1989). "Expression of immunoglobulin-T-cell receptor chimeric molecules as functional receptors with antibody-type specificity." Proc Natl Acad Sci USA 86: 10024-8.

Hafler, D. A. and Weiner, H. L. (1995). "Immunologic mechanisms and therapy in multiple sclerosis." Immunol Rev 144: 75-107.

Hernandez-Fuentes, M. P., Baker, R. J. and Lechler, R. I. (1999). "The alloresponse." Rev Immunogenet 1: 282-96.

Howe, L. R. and Weiss, A. (1995). "Multiple kinases mediate T-cell-receptor signaling." Trends Biochem Sci 20: 59-64.

Howell, M. D., Winters, S. T., Olee, T., Powell, H. C., Carlo, D. J. and Brostoff, S. W. (1989). "Vaccination against experimental allergic encephalomyelitis with T cell receptor peptides." Science 246: 668-70.

Hwu, P., Shafer, G. E., Treisman, J., Schindler, D. G., Gross, G., Cowherd, R., Rosenberg, S. A. and Eshhar, Z. (1993). "Lysis of ovarian cancer cells by human lymphocytes redirected with a chimeric gene composed of an antibody variable region and the Fc receptor gamma chain." J Exp Med 178: 361-6.

Irving, B. A. and Weiss, A. (1991). "The cytoplasmic domain of the T cell receptor zeta chain is sufficient to couple to receptor-associated signal transduction pathways." Cell 64: 891-901.

Karttunen, J. and Shastri, N. (1991). "Measurement of ligand-induced activation in single viable T cells using the lacZ reporter gene." Proc Natl Acad Sci USA 88: 3972-6.

Kaufmann, Y., Berke, G. and Eshhar, Z. (1981). "Cytotoxic T lymphocyte hybridomas that mediate specific tumor-cell lysis in vitro." Proc Natl Acad Sci USA 78: 2502-6.

Letourneur, F. and Klausner, R. D. (1991). "T-cell and basophil activation through the cytoplasmic tail of T-cell-receptor zeta family proteins." Proc Natl Acad Sci USA 88: 8905-9.

Lin, A. Y., Devaux, B., Green, A., Sagerstrom, C., Elliott, J. F. and Davis, M. M. (1990). "Expression of T cell antigen receptor heterodimers in a lipid-linked form." Science 249: 677-9.

Meinl, E., Hohlfeld, R., Wekerle, H. and Fleckenstein, B. (1995). "Immortalization of human T cells by Herpesvirus saimiri." Immunol Today 16: 55-8.

Miller, R. G., Muraoka S., Claesson, M. H., Reimann, J. and Benveniste, P. (1988). "The veto phenomenon in T-cell regulation" Ann NY Acad Sci 532: 170-6.

Mullbacher, A., Lobigs, M., Kos, F. J. and Langman, R. (1999). "Alloreactive cytotoxic T-cell function, peptide nonspecific." Scand J Immunol 49: 563-9.

Pattison, J. M. and Krensky, A. M. (1997). "New insights into mechanisms of allograft rejection." Am J Med Sci 313: 257-63.

Reich-Zeliger, S., Zhao, Y., Krauthgamer, R., Bachar-Lustig, E. and Reisner, Y. (2000). "Anti-third party CD8+ CTLs as potent veto cells: coexpression of CD8 and FasL is a prerequisite." Immunity 13: 507-15.

Roep, B. O. (1996). "T-cell responses to autoantigens in IDDM. The search for the Holy Grail." Diabetes 45: 1147-56.

Romeo, C. and Seed, B. (1991). "Cellular immunity to HIV activated by CD4 fused to T cell or Fc receptor polypeptides." Cell 64: 1037-46.

Schmidt, W., Festenstein, H., Ward, P. J. and Sanderson, A. R. (1981). "Interspecies exchange of beta 2-microglobulin and associated MHC and differentiation antigens." Immunogenetics 13: 483-91.

Sherman, L. A. and Chattopadhyay, S. (1993). "The molecular basis of allorecognition." Annu Rev Immunol 11: 385-402.

Smith, P. A., Brunmark, A., Jackson, M. R. and Potter, T. A. (1997). "Peptide-independent recognition by alloreactive cytotoxic T lymphocytes (CTL)." J Exp Med 185: 1023-33.

Stryhn, A., Pedersen, L. O., Ortiz_Navarrete, V. and Buus, S. (1994). "Preformed purified peptide/major histocompatibility class I complexes are potent stimulators of class I-restricted T cell hybridomas." Eur J Immunol 24: 1404-9.

Thomas, J. M., Carver, F. M., Cunningham, P. R, Olson, L. C. and Thomas, F. T. (1991). "Kidney allograft tolerance in primates without chronic immunosuppression—the role of veto cells." Transplantation 51: 198-207.

Uger, R. A. and Barber, B. H. (1998). "Creating CTL targets with epitope-linked beta 2-microglobulin constructs." J Immunol 160: 1598-605.

Uger, R. A, Chan, S. M. and Barber, B. H. (1999). "Covalent linkage to beta2-microglobulin enhances the MHC stability and antigenicity of suboptimal CTL epitopes." J Immunol 162: 6024-8.

Vandenbark, A. A, Chou, Y. K., Hashim, G. and Offner, H. (1991). "Immunization with T cell receptor peptides." Br J Rheumatol 30 Suppl 2: 20-3.

Wang, W., Man, S., Gulden, P. H., Hunt, D. F. and Engelhard, V. H. (1998). "Class I-restricted alloreactive cytotoxic T lymphocytes recognize a complex array of specific MHC-associated peptides." J Immunol 160: 1091-7.

Watschinger, B. (1995). "How T cells recognize alloantigen: evidence for two pathways of allorecognition." Nephrol Dial Transplant 10: 1556-8.

Weber, F., Meinl, E., Drexler, K., Czlonkowska, A., Huber, S., Fickenscher, H., Muller-Fleckenstein, I., Fleckenstein, B., Wekerle, H. and Hohlfeld, R. (1993). "Transformation of human T-cell clones by Herpesvirus saimiri: intact antigen recognition by autonomously growing myelin basic protein-specific T cells." Proc Natl Acad Sci USA 90: 11049-53.

White, J., Crawford, F., Fremont, D., Marrack, P. and Kappler, J. (1999). "Soluble class I MHC with beta2-microglobulin covalently linked peptides: specific binding to a T cell hybridoma." J Immunol 162: 2671-6.

Windhagen, A, Scholz, C., Hollsberg, P., Fukaura, H., Sette, A. and Hafler, D. A. (1995). "Modulation of cytokine patterns of human autoreactive T cell clones by a single amino acid substitution of their peptide ligand." Immunity 2: 373-80.

Wong, F. S., Karttunen, J., Dumont, C., Wen, L., Visintin, I., Pilip, I. M., Shastri, N., Pamer, E. G. and Janeway, C. A., Jr. (1999). "Identification of an MHC class I-restricted autoantigen in type I diabetes by screening an organ-specific cDNA library." Nat Med 5: 1026-31.

Wucherpfennig, K. W., Weiner, H. L. and Hafler, D. A. (1991). "T-cell recognition of myelin basic protein." Immunol Today 12: 277-82.

The invention claimed is:

1. A DNA molecule encoding a chimeric polypeptide comprising (a) a component of a MHC molecule capable of association on a cell surface with an endogenous MHC molecule component of the same class, and (b) an intracellular region of a signal transduction element capable of activating T cells, wherein said signal transduction element is a component of T cell receptor CD3 and said component of T-cell receptor CD3 comprises the transmembranal and cytoplasmic regions of the human zeta (ζ) polypeptide.

2. The DNA molecule of claim 1, wherein said MHC component (a) is a monomorphic component selected from the group consisting of β₂-microglobulin and the monomorphic α chain of a HLA-DR molecule.

3. The DNA molecule of claim 2, wherein said MHC component (a) is human β₂-microglobulin capable of association on a cell surface with an endogenous class I heavy chain HLA molecule, and said β₂-microglobulin is linked to component (b) by a bridge peptide having about 10-15 amino acid residues.

4. The DNA molecule of claim 3, wherein said bridge peptide has a sequence comprised within the membrane-proximal sequence of a class I heavy chain HLA molecule.

5. The DNA molecule of claim 4, wherein said bridge peptide has 13 amino acid residues comprised within the extracellular membrane-proximal sequence of the class I heavy chain HLA-A2 molecule, and has the sequence: Leu Arg Trp Glu Pro Ser Ser Gln Pro Thr Ile Pro Ile (SEQ ID NO:9).

6. The DNA molecule of claim 2, wherein said MHC component (a) is a monomorphic α chain of a HLA-DR molecule.

7. The DNA molecule of claim 1, wherein said MHC component (a) is a polymorphic component selected from the group consisting of: (i) an α chain of class I HLA-A, HLA-B or HLA-C molecule, which is capable of association on a cell surface with endogenous β₂m; (ii) an α chain of class II HLA-DP or HLA-DQ molecule, which is capable of association on a cell surface with endogenous HLA-DPβ or HLA-DQβ chain; or (iii) a β chain of class II HLA-DP, HLA-DR or HLA-DQ molecule, which is capable of association on a cell surface with an endogenous HLA-DPα, HLA-DRα or HLA-DQα chain.

8. The DNA molecule of claim 1, wherein said chimeric polypeptide further comprises an antigenic peptide related to an autoimmune disease, said antigenic peptide being linked to said chimeric polypeptide by a peptide linker.

9. The DNA molecule of claim 8, wherein said antigenic peptide has 8-10 amino acid residues and binds to a product of a certain HLA allele.

10. An isolated immune cell which expresses a chimeric polypeptide as defined in claim 9 and binds to an lyses autoreactive cells causing an autoimmune disease.

11. An isolated immune cell which expresses a chimeric polypeptide as defined in claim 8 and binds to and lyses autoreactive cells causing an autoimmune disease.

12. A vector comprising the DNA molecule of claim 1.

13. An isolated immune cell which expresses a chimeric polypeptide as defined in claim 1 and binds to, and eliminates, alloreactive cells causing transplant rejection.

14. The immune cell of claim 13 which is a cytotoxic T lymphocyte (CTL).

15. The cell which expresses a chimeric polypeptide comprising (a) a component of a MHC molecule capable of association on a cell surface with an endogenous MHC molecule component of the same class, and (b) an intracellular region of a signal transduction element capable of activating T cells, wherein said signal transduction element is a component of T-Cell receptor CD3 and said component of T-cell receptor CD3 comprises the transmembranal and cytoplasmic regions of the human zeta (ζ) polypeptide.

16. The cell of claim 15, wherein said cell is an immune cell selected from the group consisting of T helper cells (CD4$^+$), cytotoxic T lymphocytes (CD8$^+$) and natural killer (NK) cells, capable of recognizing and binding to harmful T cells and causing their lysis or inactivation.

* * * * *

SEQUENCE LISTING

<160> NUMBER OF SEQ ID NOS: 31

<210> SEQ ID NO 1
<211> LENGTH: 360
<212> TYPE: DNA
<213> ORGANISM: Homo sapiens

<400> SEQUENCE: 1

| | | | | | | |
|---|---|---|---|---|---|---|
| atgtctcgct | ccgtggcctt | agctgtgctc | gcgctactct | ctctttctgg | cctggagggc | 60 |
| atccagcgta | ctccaaagat | tcaggtttac | tcacgtcatc | cagcagagaa | tggaaagtca | 120 |
| aatttcctga | attgctatgt | gtctgggttt | catcaatccg | acattgaagt | tgacttactg | 180 |
| aagaatggag | agagaattga | aaaagtggag | cattcagact | tgtctttcag | caaggactgg | 240 |
| tctttctatc | tcttgtacta | cactgaattc | accccactg  | aaaaagatga | gtatgcctgc | 300 |
| cgtgtgaacc | atgtgactt  | gtcacagccc | aagatagtta | agtgggatcg | agacatgtaa | 360 |

<210> SEQ ID NO 2
<211> LENGTH: 405
<212> TYPE: DNA
<213> ORGANISM: Mus sp.

<400> SEQUENCE: 2

| | | | | | | |
|---|---|---|---|---|---|---|
| ctctgctact | tgctagatgg | aatcctcttc | atctacggag | tcatcatcac | agccctgtac | 60 |
| ctgagagcaa | aattcagcag | gagtgcagag | actgctgcca | acctgcagga | ccccaaccag | 120 |
| ctctacaatg | agctcaatct | agggcgaaga | gaggaatatg | acgtcttgga | agaagcgg   | 180 |
| gctcgggatc | cagagatggg | aggcaaacag | cagaggagga | ggaaccccca | ggaaggcgta | 240 |
| tacaatgcac | tgcagaaaga | caagatggca | gaagcctaca | gtgagatcgg | cacaaaaggc | 300 |
| gagaggcgga | gaggcaaggg | gcacgatggc | ctttaccagg | gtctcagcac | tgccaccaag | 360 |
| gacacctatg | atgccctgca | tatgcagacc | ctggcccctc | gctaa | | 405 |

<210> SEQ ID NO 3
<211> LENGTH: 819
<212> TYPE: DNA
<213> ORGANISM: Artificial
<220> FEATURE:
<223> OTHER INFORMATION: synthetic

<400> SEQUENCE: 3

| | | | | | | |
|---|---|---|---|---|---|---|
| tctagagccg | agatgtctcg | ctccgtggcc | ttagctgtgc | tcgcgctact | ctctctttct | 60 |
| ggcctggagg | gcatccagcg | tactccaaag | attcaggttt | actcacgtca | tccagcagag | 120 |
| aatggaaagt | caaatttcct | gaattgctat | gtgtctgggt | ttcatcaatc | cgacattgaa | 180 |
| gttgacttac | tgaagaatgg | agagagaatt | gaaaaagtgg | agcattcaga | cttgtctttc | 240 |
| agcaaggact | ggtctttcta | tctcttgtac | tacactgaat | tcaccccac  | tgaaaaagat | 300 |
| gagtatgcct | gccgtgtgaa | ccatgtgact | ttgtcacagc | ccagatagt  | taagtgggat | 360 |
| cgagacatgc | tgagatggga | gccctcgagc | cagcccacca | tccccatcct | ctgctacttg | 420 |
| ctagatggaa | tcctcttcat | ctacggagtc | atcatcacag | ccctgtacct | gagagcaaaa | 480 |
| ttcagcagga | gtgcagagac | tgctgccaac | ctgcaggacc | ccaaccagct | ctacaatgag | 540 |
| ctcaatctag | ggcgaagaga | ggaatatgac | gtcttggaga | agaagcgggc | tcgggatcca | 600 |
| gagatgggag | gcaaacagca | gaggaggagg | aaccccagg  | aaggcgtata | caatgcactg | 660 |
| cagaaagaca | agatggcaga | agcctacagt | gagatcggca | caaaaggcga | gaggcggaga | 720 |

```
ggcaagggc   acgatggcct   ttaccaggt   ctcagcactg   ccaccaagga   cacctatgat      780
gccctgcata   tgcagaccct   ggcccctcgc   taagaattc                                819

<210> SEQ ID NO 4
<211> LENGTH: 882
<212> TYPE: DNA
<213> ORGANISM: Artificial
<220> FEATURE:
<223> OTHER INFORMATION: synthetic

<400> SEQUENCE: 4
tctagagccg   agatgtctcg   ctccgtggcc   ttagctgtgc   tcgcgctact   ctctctttct      60
ggcctggagg   gcagtgatta   tgaagggcgg   ttgatcggag   gtggcggatc   cggaggtggt    120
tctggtggag   gttcgatcca   gcgtactcca   aagattcagg   tttactcacg   tcatccagca    180
gagaatggaa   agtcaaattt   cctgaattgc   tatgtgtctg   ggtttcatca   atccgacatt    240
gaagttgact   tactgaagaa   tggagagaga   attgaaaaag   tggagcattc   agacttgtct    300
ttcagcaagg   actggtcttt   ctatctcttg   tactacactg   aattcacccc   cactgaaaaa    360
gatgagtatg   cctgccgtgt   gaaccatgtg   actttgtcac   agcccaagat   agttaagtgg    420
gatcgagaca   tgctgagatg   ggagccctcg   agccagccca   ccatcccat   cctctgctac    480 ttgctagatg   gaatcctctt   catctacgga   gtcatcatca   cagccctgta   cctgagagca    540
aaattcagca   ggagtgcaga   gactgctgcc   aacctgcagg   accccaacca   gctctacaat    600
gagctcaatc   tagggcgaag   agaggaatat   gacgtcttgg   agaagaagcg   ggctcgggat    660
ccagagatgg   gaggcaaaca   gcagaggagg   aggaacccccc   aggaaggcgt   atacaatgca    720
ctgcagaaag   acaagatggc   agaagcctac   agtgagatcg   gcacaaaagg   cgagaggcgg    780
agaggcaagg   ggcacgatgg   cctttaccag   ggtctcagca   ctgccaccaa   ggacacctat    840
gatgccctgc   atatgcagac   cctggcccct   cgctaagaat   tc                          882

<210> SEQ ID NO 5
<211> LENGTH: 111
<212> TYPE: DNA
<213> ORGANISM: Artificial
<220> FEATURE:
<223> OTHER INFORMATION: synthetic

<400> SEQUENCE: 5
tctagagccg   agatgtctcg   ctccgtggcc   ttagctgtgc   tcgcgctact   ctctctttct      60
ggcctggagg   gctttgagag   tactggtaat   ctaattggag   gtggcggatc   c              111

<210> SEQ ID NO 6
<211> LENGTH: 114
<212> TYPE: DNA
<213> ORGANISM: Artificial
<220> FEATURE:
<223> OTHER INFORMATION: synthetic

<400> SEQUENCE: 6
tctagagccg   agatgtctcg   ctccgtggcc   ttagctgtgc   tcgcgctact   ctctctttct      60
ggcctggagg   gcctctacct   ggtgtgtggg   gagcgtggcg   gaggtggcgg   atcc            114

<210> SEQ ID NO 7
<211> LENGTH: 765
<212> TYPE: DNA
<213> ORGANISM: Homo sapiens
```

```
<400> SEQUENCE: 7
atggccataa gtggagtccc tgtgctagga ttttcatca tagctgtgct gatgagcgct      60
caggaatcat gggctatcaa agaagaacat gtgatcatcc aggccgagtt ctatctgaat    120
cctgaccaat caggcgagtt tatgtttgac tttgatggtg atgagatttt ccatgtggat    180
atggcaaaga aggagacggt ctggcggctt aagaatttg gacgatttgc cagctttgag     240
gctcaaggtg cattggccaa catagctgtg gacaaagcca acctggaaat catgacaaag    300
cgctccaact atactccgat caccaatgta cctccagagg taactgtgct cacgaacagc    360
cctgtggaac tgagagagcc caacgtcctc atctgtttca tcgacaagtt cacccccacca    420 gtggtcaatg tcacgtggct tcgaaatgga aaacctgtca ccacaggagt gtcagagaca    480
gtcttcctgc ccaggaaga ccaccttttc cgcaagttcc actatctccc cttcctgccc      540
tcaactgagg acgtttacga ctgcagggtg gagcactggg gcttggatga gcctcttctc    600
aagcactggg agtttgatgc tccaagccct ctcccagaga ctacagagaa cgtggtgtgt    660
gccctgggcc tgactgtggg tctggtgggc atcattattg ggaccatctt catcatcaag    720
ggagtgcgca aaagcaatgc agcagaacgc aggggggcctc tgtaa                    765

<210> SEQ ID NO 8
<211> LENGTH: 1041
<212> TYPE: DNA
<213> ORGANISM: Artificial
<220> FEATURE:
<223> OTHER INFORMATION: synthetic

<400> SEQUENCE: 8
ctcgaggcgc ccaagaagaa aatggccata agtggagtcc ctgtgctagg atttttcatc     60
atagctgtgc tgatgagcgc tcaggaatca tgggctatca agaagaaca tgtgatcatc     120 caggccgagt tctatctgaa tcctgaccaa tcaggcgagt ttatgtttga ctttgatggt    180
gatgagattt tccatgtgga tatggcaaag aaggagacgg tctggcggct tgaagaattt    240
ggacgatttg ccagctttga ggctcaaggt gcattggcca acatagctgt ggacaaagcc    300
aacctggaaa tcatgacaaa gcgctccaac tatactccga tcaccaatgt acctccagag    360
gtaactgtgc tcacgaacag ccctgtggaa ctgagagagc caacgtcctc catctgtttc    420
atcgacaagt tcacccccacc agtggtcaat gtcacgtggc ttcgaaatgg aaaacctgtc    480
accacaggag tgtcagagac agtcttcctg cccaggaag accacctttt ccgcaagttc     540
cactatctcc ccttcctgcc ctcaactgag gacgtttacg actgcagggt ggagcactgg    600
ggcttggatg agcctcttct caagcactgg ctctgctacc ttctagatgg aatcctcttc    660
atctacggag tcatcatcac agccctgtac ctgagagcaa aattcagcag gagtgcagag    720
actgctgcca acctgcagga ccccaaccag ctctacaatg agctcaatct agggcgaaga    780
gaggaatatg acgtcttgga gaagaagcgg gctcgggatc cagagatggg aggcaaacag    840
cagaggagga ggaaccccca ggaaggcgta caatgcac tgcagaaaga caagatggca      900
gaagcctaca gtgagatcgg cacaaaaggc gagaggcgga gaggcaaggg gcacgatggc    960
ctttaccagg gtctcagcac tgccaccaag gacacctatg atgccctgca tatgcagacc    1020
ctggcccctc gctaagaatt c                                              1041

<210> SEQ ID NO 9
<211> LENGTH: 13
<212> TYPE: PRT
<213> ORGANISM: Artificial
```

<220> FEATURE:
<223> OTHER INFORMATION: synthetic

<400> SEQUENCE: 9

Leu Arg Trp Glu Pro Ser Ser Gln Pro Thr Ile Pro Ile
1               5                   10

<210> SEQ ID NO 10
<211> LENGTH: 43
<212> TYPE: DNA
<213> ORGANISM: Artificial
<220> FEATURE:
<223> OTHER INFORMATION: synthetic

<400> SEQUENCE: 10
gctggctcga gggctcccat ctcagcatgt ctcgatccca ctt            43

<210> SEQ ID NO 11
<211> LENGTH: 30
<212> TYPE: DNA
<213> ORGANISM: Artificial
<220> FEATURE:
<223> OTHER INFORMATION: synthetic

<400> SEQUENCE: 11
gggtctagag ccgagatgtc tcgctccgtg                           30

<210> SEQ ID NO 12
<211> LENGTH: 27
<212> TYPE: DNA
<213> ORGANISM: Artificial
<220> FEATURE:
<223> OTHER INFORMATION: synthetic

<400> SEQUENCE: 12
gcggaattct tagcgagggg ccagggt                              27

<210> SEQ ID NO 13
<211> LENGTH: 48
<212> TYPE: DNA
<213> ORGANISM: Artificial
<220> FEATURE:
<223> OTHER INFORMATION: synthetic

<400> SEQUENCE: 13
gagccctcga gccagcccac catccccatc ctctgctact tgctagat       48

<210> SEQ ID NO 14
<211> LENGTH: 39
<212> TYPE: DNA
<213> ORGANISM: Artificial
<220> FEATURE:
<223> OTHER INFORMATION: synthetic

<400> SEQUENCE: 14
ctgagatggg agccgtcttc ccagcccacc atccccatc                 39

<210> SEQ ID NO 15
<211> LENGTH: 13
<212> TYPE: PRT
<213> ORGANISM: Artificial
<220> FEATURE:
<223> OTHER INFORMATION: synthetic

<400> SEQUENCE: 15

Gly Gly Gly Gly Ser Gly Gly Gly Ser Gly Gly Gly Ser

<210> SEQ ID NO 16
<211> LENGTH: 39
<212> TYPE: DNA
<213> ORGANISM: Artificial
<220> FEATURE:
<223> OTHER INFORMATION: synthetic

<400> SEQUENCE: 16
ggaggtggcg ggtccggagg tggttctggt ggaggttcg                    39

<210> SEQ ID NO 17
<211> LENGTH: 8
<212> TYPE: PRT
<213> ORGANISM: Artificial
<220> FEATURE:
<223> OTHER INFORMATION: synthetic

<400> SEQUENCE: 17

Ser Asp Tyr Glu Gly Arg Leu Ile
1               5

<210> SEQ ID NO 18
<211> LENGTH: 24
<212> TYPE: DNA
<213> ORGANISM: Influenza A virus H3N2

<400> SEQUENCE: 18
agtgattatg aagggcggtt gatc                    24

<210> SEQ ID NO 19
<211> LENGTH: 60
<212> TYPE: DNA
<213> ORGANISM: Artificial
<220> FEATURE:
<223> OTHER INFORMATION: synthetic

<400> SEQUENCE: 19
cgcggatccg ccacctccga tcaaccgccc ttcataatca ctagcctcaa ggccagaaag    60

<210> SEQ ID NO 20
<211> LENGTH: 51
<212> TYPE: DNA
<213> ORGANISM: Artificial
<220> FEATURE:
<223> OTHER INFORMATION: synthetic

<400> SEQUENCE: 20
gcgggatccg gaggtggttc tggtggaggt tcgatccagc gtactccaaa g            51

<210> SEQ ID NO 21
<211> LENGTH: 8
<212> TYPE: PRT
<213> ORGANISM: Influenza A virus

<400> SEQUENCE: 21

Phe Glu Ser Thr Gly Asn Leu Ile
1               5

<210> SEQ ID NO 22
<211> LENGTH: 24
<212> TYPE: DNA
<213> ORGANISM: Influenza A virus

```
<400> SEQUENCE: 22
tttgagagta ctggtaatct aatt                                          24

<210> SEQ ID NO 23
<211> LENGTH: 60
<212> TYPE: DNA
<213> ORGANISM: Artificial
<220> FEATURE:
<223> OTHER INFORMATION: synthetic

<400> SEQUENCE: 23
cgcggatccg ccacctccaa ttagattacc agtactctca aaagcctcaa ggccagaaag   60

<210> SEQ ID NO 24
<211> LENGTH: 9
<212> TYPE: PRT
<213> ORGANISM: Mus musculus

<400> SEQUENCE: 24

Leu Tyr Leu Val Cys Gly Glu Arg Gly
1               5

<210> SEQ ID NO 25
<211> LENGTH: 27
<212> TYPE: DNA
<213> ORGANISM: Mus musculus

<400> SEQUENCE: 25
ctctacctgg tgtgtgggga gcgtggc                                       27

<210> SEQ ID NO 26
<211> LENGTH: 63
<212> TYPE: DNA
<213> ORGANISM: Artificial
<220> FEATURE:
<223> OTHER INFORMATION: synthetic

<400> SEQUENCE: 26
cgcggatccg ccacctccgc cacgctcccc acacaccagg tagagagcct caaggccaga   60
aag                                                                 63

<210> SEQ ID NO 27
<211> LENGTH: 32
<212> TYPE: DNA
<213> ORGANISM: Artificial
<220> FEATURE:
<223> OTHER INFORMATION: synthetic

<400> SEQUENCE: 27
ggcccctcga ggcgcccaag aagaaaatgg cc                                 32

<210> SEQ ID NO 28
<211> LENGTH: 39
<212> TYPE: DNA
<213> ORGANISM: Artificial
<220> FEATURE:
<223> OTHER INFORMATION: synthetic

<400> SEQUENCE: 28
gggtctagaa ggtagcagag ccactgcttg agaagaggc                          39
```

```
<210> SEQ ID NO 29
<211> LENGTH: 25
<212> TYPE: DNA
<213> ORGANISM: Artificial
<220> FEATURE:
<223> OTHER INFORMATION: synthetic

<400> SEQUENCE: 29
gggtctagat ggaatcctct tcatc                                            25

<210> SEQ ID NO 30
<211> LENGTH: 28
<212> TYPE: DNA
<213> ORGANISM: Artificial
<220> FEATURE:
<223> OTHER INFORMATION: synthetic

<400> SEQUENCE: 30
cgcgcctcga gcccctggtc ctgtcctg                                         28

<210> SEQ ID NO 31
<211> LENGTH: 20
<212> TYPE: DNA
<213> ORGANISM: Artificial
<220> FEATURE:
<223> OTHER INFORMATION: synthetic

<400> SEQUENCE: 31
gtaatgtgtt tgtcatacag                                                  20
```